United States Patent
Chen et al.

(10) Patent No.: US 11,884,974 B2
(45) Date of Patent: Jan. 30, 2024

(54) TIM-3 NANOBODY, A PREPARATION METHOD THEREOF, AND USE THEREOF

(71) Applicant: Shihezi University, Xinjiang (CN)

(72) Inventors: Chuangfu Chen, Xinjiang (CN); Peng Wu, Xinjiang (CN)

(73) Assignee: Shihezi University, Xinjiang (CN)

( * ) Notice: Subject to any disclaimer, the term of this patent is extended or adjusted under 35 U.S.C. 154(b) by 545 days.

(21) Appl. No.: 16/919,500

(22) Filed: Jul. 2, 2020

(65) Prior Publication Data

US 2021/0002699 A1    Jan. 7, 2021

(30) Foreign Application Priority Data

Jul. 5, 2019 (CN) .......................... 201910604220.8
Mar. 9, 2020 (CN) .......................... 202010157316.7

(51) Int. Cl.
  *C07K 16/28* (2006.01)
  *C12Q 1/686* (2018.01)
  *C12Q 1/6886* (2018.01)

(52) U.S. Cl.
  CPC .......... *C12Q 1/686* (2013.01); *C07K 16/2803* (2013.01); *C12Q 1/6886* (2013.01); *C07K 2317/569* (2013.01); *C07K 2317/76* (2013.01)

(58) Field of Classification Search
  CPC .. C12Q 1/686; C12Q 1/6886; C07K 16/2803; C07K 2317/569; C07K 2317/76
  USPC ........................................................ 435/6.12
  See application file for complete search history.

(56) References Cited

PUBLICATIONS

Vincke et al. "Introduction to heavy chain antibodies and derived nanobodies." Methods Mol Biol (2012) 911:15-26. doi: 10.1007/978-1-61779-968-6_2 (Year: 2012).*

* cited by examiner

*Primary Examiner* — Aaron A Priest
*Assistant Examiner* — Randi Lynn Beil
(74) *Attorney, Agent, or Firm* — Nitin Kaushik

(57) ABSTRACT

The application belongs to the technical field of animal or human antibodies, and discloses a TIM-3 nanobody, a preparation method thereof and use thereof. The nanobody is a TIM-3 nanobody with sequence of SEQ ID NO:1. TIM-3 antigen is a transient transfection expression by mammalian cells. TIM-3 antigen is used to screen the nanobody library repeatedly, specific phage of nanobody is obtained, and the target fragment is conducted sequencing. The application uses the HEK293 cell line to express antigen. Using the mammalian expression system to express human protein may maximumly guarantee the original structure of the protein, guarantee the protein to have a post-translational modification and specific modifications of eukaryotic proteins such as glycosylation, which makes the obtained protein have high activity. This method maximizes the original structure and activity of the protein; the nanobodies screened by the application can efficiently and specifically bind to the target.

<110> Shihezi University
<120> TIM-3 nanobody, a preparation method thereof, and use thereof
<160> 3
<210> 1
<211> 1049
<212> DNA
<213> Artificial Sequence
<400> 1
GGTGGGCGGA   CATTTCACAA   GCTTAAGGAG
  ACAGTACATA   TGAAATACCT   ATTGCCTACG (Continued)

GCAGCCGCTG GATTGTTATT ACTCGCGGCC
CAGCCGGCCA TGGCCCAGGT GCAGCTGCAG
GAGTCTGGAG GAGGCTTGGT GCAGCCTGGG
GGGTCTCTGA GACTCTCCTG TGCAGCCTCT
GGGTTCACCT TCCGTAGATC TATTCTGAAA
TGGCTCCGAC AGGCTCCAGG GAAGGAACTG
GAGTGGGTGT CCACTATAGA TACATACTCT
AATAACACAT ACTATGAAGA CTCCTTGAAG
GGCCGATTCA CCATCTCCGC AGACAACGCC
AAGAACACGC TGTATCTGCA AATGGACAGC
CTGAAACCTG AGGACACGGC CGTGTATTAC
TGTGCAAAGG GTGGAGGTGG TATCTACTCC
CGCACGTATG ACTACCGGGG CCAGGGGACC
CAGGTCACCG TCTCCTCAGC GGCCGCATAC
CCGTACGACG TTCCGGACTA CGGTTCCCAC
CACCATCACC ATCACTAGAC TGTTGAAAGT
TGTTTAGCAA AACCTCATAC AGAAAATTCA
TTTACTAACG TCTGGAAAGA CGACAAAACT
TTAGATCGTT ACGCTAACTA TGAGGGCTGT
CTGTGGAATG CTACAGGCGT TGTCGTTTGT
ACTGGTGACG AAACTCAGTG TTACGGTACA
TGGGTTCCTA TTGGGCTTGC TATCCCTGAA AAT-
GAGGGTG GTGGCTCTGA GGGTGGCGGT TCT-
GAGGGTG GCGGTTCTGA GGGTGGCGGT ACT-
AAACCTC CTGAGTACGG TGATACACCT
ATTCCGGGCT ATACTTATAT CAACCCTCTC
GACGGCACTT ATCCGCCTGG TACTGAGCAA
AACCCCGCTA ATCCTAATCC CTTCTCTTGA
GGAGTCTCAG CCTCTTATAC TTTCATGTTT
CAGATATAGG TTCCGAAATA GGCAGGTGCA
TTAACTGTTA TACGGGCACT GTACTCATGC
ACTGACCCCG TTAAACTTAT TACCAGTACA
CTCCTGTATC ATCAAAAGCC ATGTATGA
<210> 2
<211> 30
<212> DNA
<213> Artificial Sequence
<400> 2
GACACGAATTCGCCACCATGTTCAGCCACC
<210> 3
<211> 35
<212> DNA
<213> Artificial Sequence
<400> 3
GTGTCAAGCTTTCACTTGTCATCATCATCCTTGTA
<210> 4
<211> 4541
<212> DNA
<213> Unknown
<400> 4
GAGCGCCCAA TACGCAAACC GCCTCTCCCC
GCGCGTTGGC CGATTCATTA ATGCAGCTGG
CACGACAGGT TTCCCGACTG GAAAGCGGGC
AGTGAGCGCA ACGCAATTAA TGTGAGTTAG
CTCACTCATT AGGCACCCCA GGCTTTACAC
TTTATGCTTC CGGCTCGTAT GTTGTGTGGA
ATTGTGAGCG GATAACAATT TCACACAGGA
AACAGCTATG ACCATGATTA CGCCAAGCTT
GCATGCAAAT TCTATTTCAA GGAGACAGTC
ATAATGAAAT ACCTATTGCC TACGGCAGCC
GCTGGATTGT TATTACTCGC GGCCCAGCCG
GCCATGGCCC AGGTGCAGCT GCAGGAGTCT
AGAGGGGACC CAGGTCACCG TCTCCTCAGC
GGCCGCATAC CCGTACGACG TTCCGGACTA
CGGTTCCCAC CACCATCACC ATCACTAGAC TGTTGAAAGT TGTTTAGCAA AACCTCATAC
AGAAAATTCA TTTACTAACG TCTGGAAAGA
CGACAAAACT TTAGATCGTT ACGCTAACTA
TGAGGGCTGT CTGTGGAATG CTACAGGCGT
TGTGGTTTGT ACTGGTGACG AAACTCAGTG
TTACGGTACA TGGGTTCCTA TTGGGCTTGC
TATCCCTGAA AATGAGGGTG GTGGCTCTGA
GGGTGGCGGT TCTGAGGGTG GCGGTTCTGA
GGGTGGCGGT ACTAAACCTC CTGAGTACGG
TGATACACCT ATTCCGGGCT ATACTTATAT
CAACCCTCTC GACGGCACTT ATCCGCCTGG
TACTGAGCAA AACCCCGCTA ATCCTAATCC
TTCTCTTGAG GAGTCTCAGC CTCTTAATAC TTT-
CATGTTT CAGAATAATA GGTTCCGAAA
TAGGCAGGGT GCATTAACTG TTTATACGGG
CACTGTTACT CAAGGCACTG ACCCCGTTAA
AACTTATTAC CAGTACACTC CTGTATCATC
AAAAGCCATG TATGACGCTT ACTGGAACGG
TAAATTCAGA GACTGCGCTT CCATTCTGG CTT-
AATGAG GACCCATTCG TTTGTGAATA
TCAAGGCCAA TCGTCTGACC TGCCTCAACC
TCCTGTCAAT GCTGGCGGCG GCTCTGGTGG
TGGTTCTGGT GGCGGCTCTG AGGGTGGCGG
CTCTGAGGGT GGCGGTTCTG AGGGTGGCGG
CTCTGAGGGT GGCGGTTCCG GTGGCGGCTC
CGGTTCCGGT GATTTTGATT ATGAAAAAAT
GGCAAACGCT AATAAGGGGG CTATGACCGA
AAATGCCGAT GAAAACGCGC TACAGTCTGA
CGCTAAAGGC AAACTTGATT CTGTCGCTAC
TGATTACGGT GCTGCTATCG ATGGTTTCAT
TGGTGACGTT TCCGGCCTTG CTAATGGTAA
TGGTGCTACT GGTGATTTTG CTGGCTCTAA
TTCCCAAATG GCTCAAGTCG GTGACGGTGA
TAATTCACCT TTAATGAATA ATTTCCGTCA ATATT-
TACCT TCTTTGCCTC AGTCGGTTGA
ATGTCGCCCT TATGTCTTTG GCGCTGGTAA
ACCATATGAA TTTTCTATTG ATTGTGACAA
AATAAACTTA TTCCGTGGTG TCTTTGCGTT
TCTTTTATAT GTTGCCACCT TTATGTATGT
ATTTTCGACG TTTGCTAACA TACTGCGTAA
TAAGGAGTCT TAATAAGAAT TCACTGGCCG
TCGTTTTACA ACGTCGTGAC TGGGAAAACC
CTGGCGTTAC CCAACTTAAT CGCCTTGCAG
CACATCCCCC TTTCGCCAGC TGGCGTAATA
GCGAAGAGGC CCGCACCGAT CGCCCTTCCC
AACAGTTGCG CAGCCTGAAT GGCGAATGGC
GCCTGATGCG GTATTTTCTC CTTACGCATC
TGTGCGGTAT TCACACCGC ATATAAATTG
TAAACGTTAA TATTTTGTTA AAATTCGCGT
TAAATTTTTG TTAAATCAGC TCATTTTTTA
ACCAATAGGC CGAAATCGGC AAAATCCCTT
ATAAATCAAA AGAATAGCCC GAGATAGGGT
TGAGTGTTGT TCCAGTTTGG AACAAGAGTC
CACTATTAAA GAACGTGGAC TCCAACGTCA
AAGGGCGAAA AACCGTCTAT CAGGGCGATG
GCCCACTACG TGAACCATCA CCCAAATCAA
GTTTTTTGGG GTCGAGGTGC CGTAAAGCAC
TAAATCGGAA CCCTAAAGGG AGCCCCCGAT
TTAGAGCTTG ACGGGGAAAG CCGGCGAACG
TGGCGAGAAA GGAAGGGAAG AAAGCGAAAG
GAGCGGGCGC TAGGGCGCTG GCAAGTGTAG
CGGTCACGCT GCGCGTAACC ACCACACCCG
CCGCGCTTAA TGCGCCGCTA CAGGGCGCGT ACT-
ATGGTTG CTTTGACGGG TGCACTCTCA GTA-
CAATCTG CTCTGATGCC GCATAGTTAA GCCAGCCCCG ACACCCGCCA ACACCCGCTG
ACGCGCCCTG ACGGGCTTGT CTGCTCCCGG
CATCCGCTTA CAGACAAGCT GTGACCGTCT
CCGGGAGCTG CATGTGTCAG AGGTTTTCAC
CGTCATCACC GAAACGCGCG AGACGAAAGG
GCCTCGTGAT ACGCCTATTT TTATAGGTTA ATGT-
CATGAT AATAATGGTT TCTTAGACGT
CAGGTGGCAC TTTTCGGGGA AATGTGCGCG
GAACCCCTAT TTGTTTATTT TTCTAAATAC ATT-
CAAATAT GTATCCGCTC ATGAGACAAT AACCCT-
GATA AATGCTTCAA TAATATTGAA
AAAGGAAGAG TATGAGTATT CAACATTTCC
GTGTCGCCCT TATTCCCTTT TTTGCGGCAT
TTTGCCTTCC TGTTTTTGCT CACCCAGAAA
CGCTGGTGAA AGTAAAAGAT GCTGAAGATC
AGTTGGGTGC ACGAGTGGGT TACATCGAAC
TGGATCTCAA CAGCGGTAAG ATCCTTGAGA
GTTTTCGCCC CGAAGAACGT TTTCCAATGA
TGAGCACTTT TAAAGTTCTG CTATGTGGCG
CGGTATTATC CCGTATTGAC GCCGGGCAAG
AGCAACTCGG TCGCCGCATA CACTATTCTC
AGAATGACTT GGTTGAGTAC TCACCAGTCA
CAGAAAAGCA TCTTACGGAT GGCATGACAG
TAAGAGAATT ATGCAGTGCT GCCATAACCA
TGAGTGATAA CACTGCGGCC AACTTACTTC
TGACAACGAT CGGAGGACCG AAGGAGCTAA
CCGCTTTTTT GCACAACATG GGGGATCATG
TAACTCGCCT TGATCGTTGG GAACCGGAGC
TGAATGAAGC CATACCAAAC GACGAGCGTG
ACACCACGAT GCCTGTAGCA ATGGCAACAA
CGTTGCGCAA ACTATTAACT GGCGAACTAC
TTACTCTAGC TTCCCGGCAA CAATTAATAG
ACTGGATGGA GGCGGATAAA GTTGCAGGAC
CACTTCTGCG CTCGGCCCTT CCGGCTGGCT
GGTTTATTGC TGATAAATCT GGAGCCGGTG
AGCGTGGGTC TCGCGGTATC ATTGCAGCAC
TGGGGCCAGA TGGTAAGCCC TCCCGTATCG
TAGTTATCTA CACGACGGGG AGTCAGGCAA
CTATGGATGA ACGAAATAGA CAGATCGCTG AGA-
TAGGTGC CTCACTGATT AAGCATTGGT
AACTGTCAGA CCAAGTTTAC TCATATATAC TTTA-
GATTGA TTTAAAACTT CATTTTTAAT
TTAAAAGGAT CTAGGTGAAG ATCCTTTTTG
ATAATCTCAT GACCAAAATC CCTTAACGTG
AGTTTTCGTT CCACTGAGCG TCAGACCCCG
TAGAAAAGAT CAAAGGATCT TCTTGAGATC
CTTTTTTTCT GCGCGTAATC TGCTGCTTGC
AAACAAAAAA ACCACCGCTA CCAGCGGTGG
TTTGTTTGCC GGATCAAGAG CTACCAACTC
TTTTTCCGAA GGTAACTGGC TTCAGCAGAG
CGCAGATACC AAATACTGTC CTTCTAGTGT
AGCCGTAGTT AGGCCACCAC TTCAAGAACT
CTGTAGCACC GCCTACATAC CTCGCTCTGC
TAATCCTGTT ACCAGTGGCT GCTGCCAGTG
GCGATAAGTC GTGTCTTACC GGGTTGGACT
CAAGACGATA GTTACCGGAT AAGGCGCAGC
GGTCGGGCTG AACGGGGGGT TCGTGCACAC
AGCCCAGCTT GGAGCGAACG ACCTACACCG
AACTGAGATA CCTACAGCGT GAGCATTGAG
AAAGCGCCAC GCTTCCCGAA GGGAGAAAGG
CGGACAGGTA TCCGGTAAGC GGCAGGGTCG
GAACAGGAGA GCGCACGAGG GAGCTTCCAG
GGGGAAACGC CTGGTATCTT TATAGTCCTG
TCGGGTTTCG CCACCTCTGA CTTGAGCGTC GAT-
TTTTGTG ATGCTCGTCA GGGGGGCGGA GCC-
TATGGAA AAACGCCAGC AACGCGGCCT TTT-
TACGGTT CCTGGCCTTT TGCTGGCCTT
TTGCTCACAT GTTCTTTCCT GCGTTATCCC
CTGATTCTGT GGATAACCGT ATTACCGCCT
TTGAGTGAGC TGATACCGCT CGCCGCAGCC
GAACGACCGA GCGCAGCGAG TCAGTGAGCG
AGGAAGCGGAA 2 Claims, 10 Drawing Sheets Specification includes a Sequence Listing.

```
HindIII                                                        NcoI
aagcttaaggagacagtacat atgaaatacctattg // ccggccatggcc
                     <<........pelB.. // ..........>>
                       m  k  y  l  l  //  p  a  m  a
      PstI      XbaI              Eco91I              NotI
caggtgcagctgcaggagtctagagggacccaggtcaccgtctcctcagcggccgca
<<.......VHH...............————........VHH........>>
  q  v  q  l  q                   g  t  q  v  t  v  s  s  a  a
tacccgtacgacgttccggactacggttcc caccaccatcaccatcac tag act..
>>.........HA-tag............>> <<....His-tag...>>   Gene3
  y  p  y  d  v  p  d  y  g  s  h  h  h  h  h  h   x  t
```
FIG.5
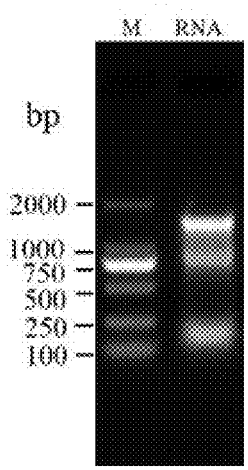
FIG.6
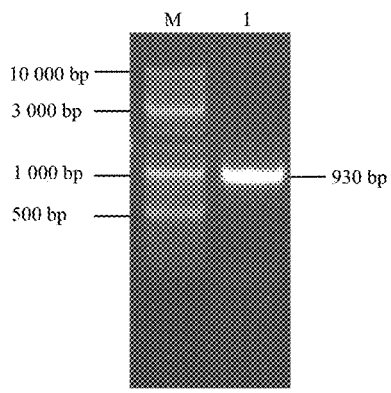
FIG.7

TIM-3 NANOBODY, A PREPARATION METHOD THEREOF, AND USE THEREOF

CROSS REFERENCE TO RELATED APPLICATION

This application claims the priority of Chinese Patent Application No. 202010157316.7 entitled "TIM-3 nanobody, a preparation method thereof, and use thereof" filed with the Chinese Patent Office on Mar. 9, 2020, which is incorporated herein by reference in its entirety.

SEQUENCE LISTING

The sequence listing file submitted herewith, named "WIUS236342P_SeqList_ST25.TXT", created on Aug. 21, 2023, and having a file size of 8,268 bytes, is incorporated by reference herein.

TECHNICAL FIELD

The present application belongs to the technical field of antibody to animals or people, especially relates to a TIM-3 nanobody, a preparation method thereof, and use thereof.

BACKGROUND ART

At present, T-cell immunoglobulinandmucin-3 (hereinafter short for TIM-3) is a membrane protein, which is a new member of the T-cell immunoglobulin family. TIM-3 was first found in Th1 type lymphocytes and $CD8^+$ T lymphocytes. The mouse derived TIM-3 coding gene exists on chromosome 11, which is highly similar to the human TIM-3 coding gene, while the human TIM-3 coding gene exists on chromosome 5 and contains 7 exons.

It is suggested that TIM-3 is selectively expressed on activated Th1 cells and can be used as a new marker to differentiate Th1 cells from Th2 cells. TIM-3 can inhibit Th1 cells by binding to its ligand, participates in the occurrence of inflammation, regulates the activation and function of immune cells, and plays a very important role in the response to many diseases. It can also be expressed on non-Th1 cells and perform different biological functions. When TIM-3 is combined with Bat3, its activity is inhibited. Th1-specific transcription factor T-bet can regulate the expression of TIM-3, and T-bet can directly bind to the promoter of TIM-3. TIM-3 can regulate the functions of Th1 and Th2 cells, and the occurrence of various diseases is also related to its abnormal expression, so it is considered as an important gene related to body diseases.

There is an essential logical difference between bio-immunotherapy and conventional chemotherapy or targeted therapy: "immunotherapy" targets immune cells (or the immune system), not cancer cells. In cancer immunotherapy, suppression of the immune checkpoint pathway is considered as one of the most promising treatments. The mechanism is to release the suppressed activity state of T-cells by inhibiting the relevant targets in the pathway, and the activated T-cells can attack and eliminate tumor cells. Antibodies do not act directly on tumor cells, but kill tumor cells indirectly by acting on T-cells. In addition, they do not target specific substances on the tumor's surface, but systematically enhance the anti-tumor immune response throughout the body. TIM-3 target and TIM-3 monoclonal antibody are hot spots in biological immunotherapy.

Nanobody was first reported in the journal Nature by Belgian scientists in 1993. There is antibody with natural loss of light chains in the peripheral blood of the alpaca. The antibody only contains one heavy chain variable region (VHH) and two conventional CH2 and CH3 regions, but it is unlike the artificially modified single antibody fragments (scFv) to be viscous easily with each other, or even aggregate into blocks. More importantly, the VHH structure produced by independent cloning and subsequently expressing has the structural stability and antigen-binding activity equivalent to that of the original heavy chain antibody, and is the smallest unit known to bind target antigen. VHH crystals are 2.5 nm in width and 4 nm in length, and of a molecular weight of only 15 KD, hence they are also called Nanobody (Nb). In conclusion, the problems with prior art are as follows:

(1) The existing monoclonal antibodies are heterologous to the human body due to problems such as a large molecular mass of 150 ku and mouse origin. Mouse monoclonal antibody, if applies in human body, will produce anti-mouse monoclonal antibody, which can not be applied repeatedly, and thus affecting its efficacy.

(2) The existing monoclonal antibodies are relatively large in volume and cannot enter into tumor tissues properly. The monoclonal antibody has a long development cycle, high production cost and low output. The monoclonal antibody drugs are expensive in price, complicated in development and humanization, and limited in success rate.

(3) The existing monoclonal antibodies are difficult to produce on a large scale, since the cost of the construction of a factory for producing monoclonal antibody drugs and the production of the drugs are huge.

(4) The existing monoclonal antibodies are unstable, easy to degrade and thus leading to high conservation cost, easy to pollute and thus leading to expensive maintenance cost. It will decompose under conditions of high temperature and strong acids and bases, so it must be kept at low temperature, otherwise it will become completely inactive within a few weeks. Antibodies are quickly degraded by the digestive system, preventing them from reaching the brain or other active sites.

The difficulty in solving the above problems: The nanobody contains 3 hypervariable regions, all of which are on the same side, and 4 framework regions. The nanobodies have a structure similar to that of a human antibody VH, sequencing shows an extremely homology with VH3, but the CDR1(complementarity-determining region-1) and CDR3(complementarity-determining region-3) of the nanobodies are relatively long. The CDR3 of nanobody has a protruded portion, which can increase the affinity of binding to antigens. The nanobody has a stable structure, which guarantees the stability of binding. Phage display technology is the most popular way to produce nanobody, which introduce the sequences of nanobody into the phage sequences, subsequently the target protein expresses on the phage shell. Phage library construction is achieved by immunization of camelids, which comprises the steps of obtaining the animal leukocytes, reverse transcribing to RNA (extracting the total ribonucleic acid (RNA) of lymphocytes and reverse transcribing it into cDNA), and thus obtaining the construction of a library against the antigen. Significance of solving the technical problems above: the Chinese Academy of Medical Sciences has developed a "monoclonal antibody-drug" conjugate with targeted and selective killing of tumor cells. The conjugate uses a monoclonal antibody as a "carrier" and carries the drug to precisely bind to tumor cells, which can kill cancer cells in situ without damaging other normal cells. The synthetic drug

SUMMARY OF THE INVENTION

According to the problems existing in the prior art, the application provides a TIM-3 antigen, a nanobody, a screening and identification method thereof, and use thereof. Nanobody can maintain its conformation in harsh environment. It has great heat resistance, and can be stored at room temperature for more than a week. And the super acid and alkali resistance allows the nanobody to well resist different environments, and increase the application range of the nanobody. The small size of the single-domain heavy chain antibody also makes it less immunogenic and makes it possible for animals to inject protein for a long periods of time. The binding sites of nanobody to antigens are also different from monoclonal antibodies, and the binding sites can be a place where traditional antibodies can never reach. Nanobody can also be produced by using prokaryotic expression, which can greatly reduce the production cost. The application is realized as follows: a nanobody, the nanobody is a TIM-3 nanobody, with a sequence of SEQ ID NO:1.

Another purpose of the application is to provide a TIM-3 antigen expressing the nanobody, which is expressed by transient transfection of mammalian cells. The TIM-3 antigen is used for multiple screening of the nanobody library to obtain specific nanobody phages, and thus obtaining the target fragment through sequencing.

Another purpose of the application is to provide a screening and identification method of the nanobody, the screening and identification method comprises the steps of:

S1, vector construction: amplifying a target fragment, digesting the target fragment and the vector with an enzyme, connecting the target fragment with the vector, transforming, screening clones;

S2, protein identification;

S3, antibody library construction: extracting the total RNA in a sample and synthesizing cDNA, preparing fragments for VHH library, conducting an electro transformation, and constructing the library.

Further, the amplifying the target fragment in S1 is specifically as follows:

(1) designing and synthesizing 2 primers, amplifying by PCR the sufficient target products; the primers sequences are: SEQ ID NO:2, SEQ ID NO:3;

(2) the enzyme used in the PCR is Pfu high temperature polymerase.

Further, the amount of each ingredient in the PCR in S1 is as follows: primer concentration: 10D dissolved in 400 µl ddH$_2$O; reaction system: 50 µl; primer mix, (½s) 0.4 µl×13.6, 8 µl in total; 10× pfu Buffer: 5 µl; each of the upstream primer and downstream primer: 2 µl; Pfu: 0.4 µl(5µ/µl); ddH$_2$O: replenishing water to 50 µl respectively.

The specific steps of the PCR amplifying of the target fragment are as follows:

(1) the first round PCR procedure:

$$\left.\begin{array}{l}95°\text{ C. 3 min}\\95°\text{ C. 22 sec}\\50°\text{ C. 20 sec}\\72°\text{ C. 40 sec}\\72°\text{ C. 5 min}\end{array}\right\} 18 \text{ cyc.}$$

The above is the first round PCR reaction system, the products of the first round PCR are used as the template prepared for the second round PCR.

(2) the second round PCR system:

The amount of each ingredient in the second round PCR is as follows: primer concentration: 10D dissolved in 400 µl ddH$_2$O; the upstream primer-1: 2 µl; the down stream primer-28: 2 µl; products of the first round PCR procedure: 1 µl; dNTP: 1 µl (25 mM each); 10× pfu Buffer: 5 µl; Pfu: 0.4 µl (5µ/µl); ddH$_2$O: replenishing water to 50 µl respectively;

(3) the second round PCR procedure:

$$\left.\begin{array}{l}95°\text{ C. 3 min}\\95°\text{ C. 22 sec}\\55°\text{ C. 20 sec}\\72°\text{ C. 45 sec}\\72°\text{ C. 5 min}\end{array}\right\} 22 \text{ cyc.}$$

Conducting agarose gel electrophoresis for the products from the second PCR, collecting the purified fragments and preparing for digestion.

Further, the steps of digesting the PCR products in S1 with enzyme are as follows:

The enzyme digestion system of the PCR fragment products is as follows: 50 µl in total; purified and collected fragments: 1 µg(20 µl); 10×FD Buffer: 5 µl; EcoRI: 1 µl(10µ/µl); HindIII: 1 µl(10µ/µl); ddH$_2$O: 23 µl;

The enzyme digestion system of the vector is as follows: PCDNA3.1+: 1 µg; 10×FD Buffer: 5 µl; EcoRI: 1 µl(10µ/µl); HindIII: 1 µl(10µ/µl); ddH$_2$O: 42 µl; keeping the systems in a 37° C. thermostat water bath reacting for 2 h, collecting the digested vector and fragments;

The steps of connecting the target fragments with the vector in S1 is connecting the collected and purified target DNA fragments with the vector; the connecting system is as follows: 20 µl in total; target fragments of the enzyme: 8 µl; digestion vector of PCDNA3.1+: 4 µl; 10×T4 DNA ligase Buffer 2 µl(5µ/µl); T4 DNA ligase: 1 µl (5µ/µl), ddH$_2$O: replenishing to 20 µl;

The specific operation of transforming, screening clones: keeping the mixture for connecting in a 22° C. PCR Instrument for 1 h.

Further, the steps of preparing fragments for VHH library, electro transformation and constructing the library are as follows: using a M13 phage display system to display the VHH antibody library, which is composed of pMECS phagemid vector, *E. coli* TG1 and M13KO7 helper phages; in the pMECS phagemid vector, the sequence before the Pst I restriction site is the coding sequence of the pelB secreting signal peptide and part of the amino acid in the first framework region of the antibody, pelB secreting signal peptide may guide the subsequent peptides to be secreted into the periplasmic cavity; the Not I restriction site is followed by the HA and 6×His labeled coding sequences for purification or detection of fusion proteins.

Another purpose of the application is to provide a nanobody in the use of binding the human targets to block a signal pathway.

Another purpose of the application is to provide a nanobody in the use of preparing the reagents for tumor detection or treatment. A use of the nanobody in preparing immune adjuvants that enhance animal immunity or immunostimulants with the virus and/or bacteria spreading.

From the above, the advantages and the positive effects are as follows: TIM-3 antigen in the application is expressed by transient transfection of mammalian cells. Alpacas are used for immunized animals. Biotinylation is used for screening. The nanobody fragments obtained by screening have their own unique gene sequences. The antibody may be used in binding the human targets to block a signal pathway, in treating or detecting tumor. Amplifying target fragment, digesting the target fragment and vector with an enzyme, connecting the target fragment with the vector, transforming, screening clones; expressing and identifying the protein; antibody library construction: extracting the total RNA in a sample and synthesizing cDNA, preparing VHH library fragment, conducting the electro transformation, and constructing the library; using a M13 phage display system to display the VHH antibody library, which is composed of pMECS phagemid vector, E. coli TG1 and M13KO7 helper phages; in the pMECS phagemid vector, the sequence before the Pst I restriction site is the coding sequence of the pelB secreting signal peptide and part of the amino acid in the first framework region of the antibody, pelB secreting signal peptide may guide the subsequent peptides to be secreted into the periplasmic cavity; the Not I restriction site is followed by the HA and 6×His labeled coding sequences for purification or detection of fusion proteins. Specific nanobody phages are obtained by multiple screening of nanobody library using antigens, and the target fragment is obtained by sequencing.

The binding site of the nanobody and the antigen is different from that of monoclonal antibody. Using nanobody to replace monoclonal antibody may improve or synergistically enhance the binding ability with the antigen. The nanobody does not have a complete antibody structure, because of lacking the Fc-end and Y-type structure, so the nanobody is not easy to be recognized and may easily escape the capture by the immune system.

The application uses the HEK293 cell line to express antigen, and using of the mammalian expression system to express human protein may maximumly guarantee the original structure of the protein, guarantee the protein with a post-translational modification and specific modifications of eukaryotic proteins such as glycosylation, which makes the obtained protein have high activity. This method maximizes the original structure and activity of the protein.

The application uses alpaca as an immunized animal may better protect and save the amount of antigen. The nanobody screened by this method may bind to the target with high efficiency and specificity.

BRIEF DESCRIPTION OF THE DRAWINGS

FIG. 5 is a schematic diagram of a nucleotide sequence of SEQ ID NO:4 of an embodiment coding a phage PIII capsid protein.

FIG. 6 is a gel electrophoresis of total RNA sample of an embodiment.

FIG. 7 is a schematic diagram of the PD-1 PCR amplification results of an embodiment.

In the diagram: M.DL-10 000 Marker; 1. objective band.

Figure 8:
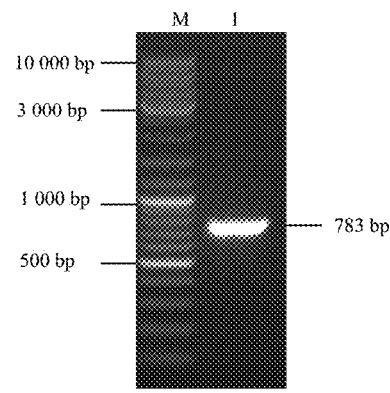

FIG. 8 is a schematic diagram of the PD-L1 PCR amplification results of an embodiment.

In the diagram: M.DL-10 000 Marker; 1. objective band.

Figure 9:
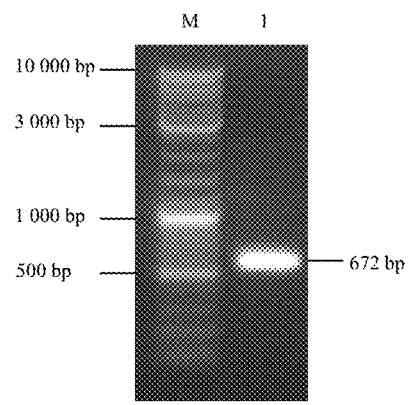

FIG. 9 is a schematic diagram of the TIM-3 PCR amplification results of an embodiment.

In the diagram: M.DL-10 000 Marker; 1. objective band.

Figure 10:
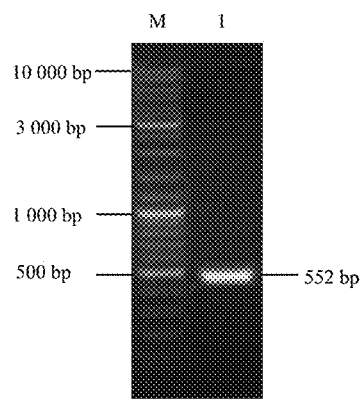

FIG. 10 is a schematic diagram of the CTLA-4 PCR amplification results of an embodiment.

In the diagram: M.DL-10 000 Marker; 1. objective band.

Figure 11:
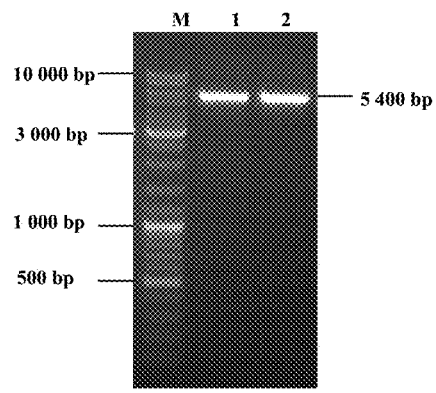

FIG. 11 is a schematic diagram of the results of enzyme digestion identification of an embodiment. In the diagram: 1,2.pcDNA3.1 enzyme digested bands; M.DL-10 000 Marker.

Figure 12:
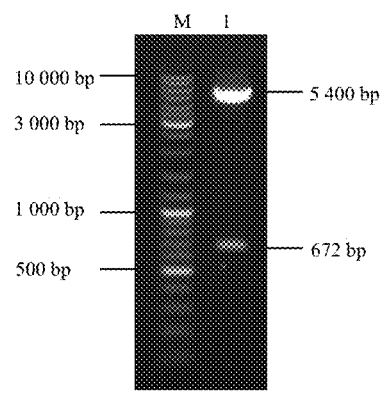

FIG. 12 is a schematic diagram of the identification results of enzyme digestion of TIM-3 of an embodiment.

In the diagram: M.DL-10 000 Marker; 1. objective band.

Figure 13:
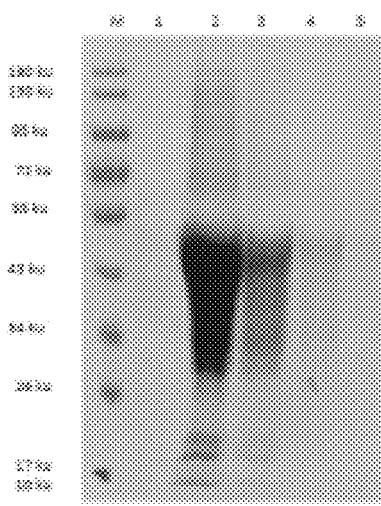

FIG. 13 is a schematic diagram of the SDS-PAGE detection results of TIM-3 of an embodiment.

Figure 14:
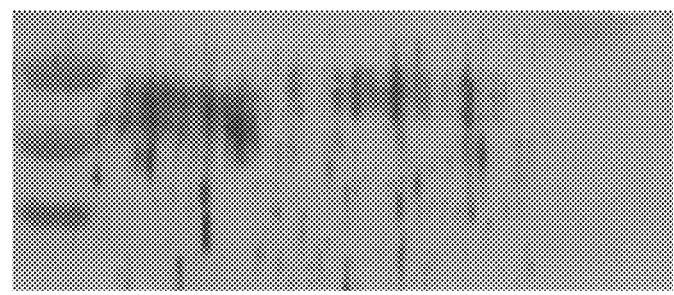

FIG. 14 is a schematic diagram of the detection results of TIM-3 specific WB of an embodiment.

Figure 15:
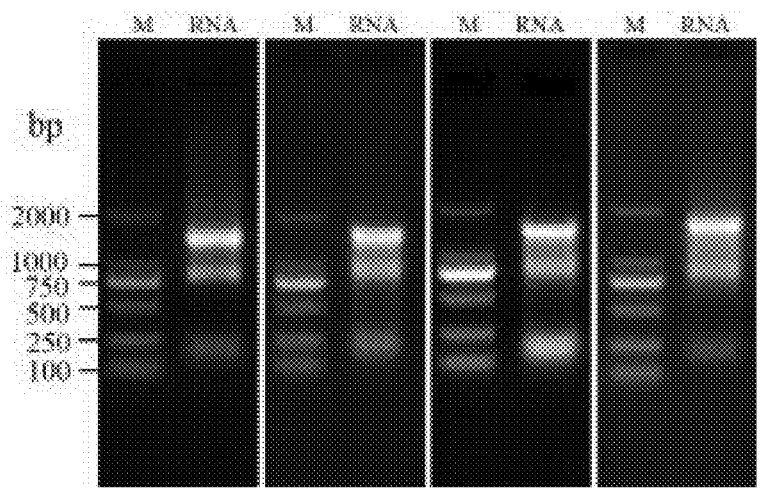

FIG. 15 is a gel electrophoresis diagram of total RNA sample gel of an embodiment.

Figure 16A:
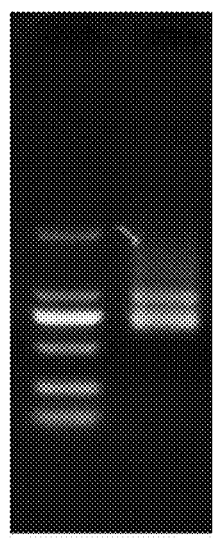
Figure 16B:
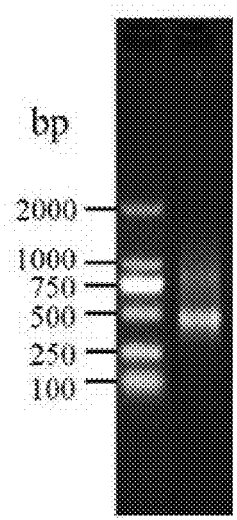

FIG. 16-A is a schematic diagram of electrophoresis analyses of the 1st PCR amplified products of TIM-3 camel antibody fragment of an embodiment.

FIG. 16-B is a schematic diagram of electrophoresis analyses of the 2nd PCR amplified products of TIM-3 camel antibody fragment of an embodiment.

Figure 17:
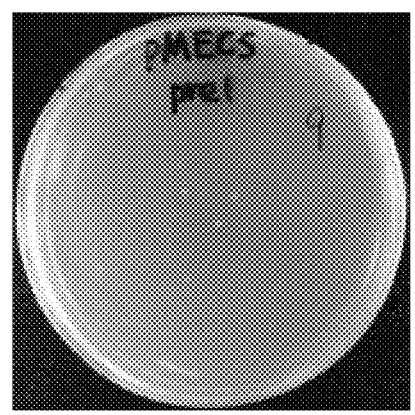

FIG. 17 is a schematic diagram of the vector self-connection test of an embodiment.

Figure 18:
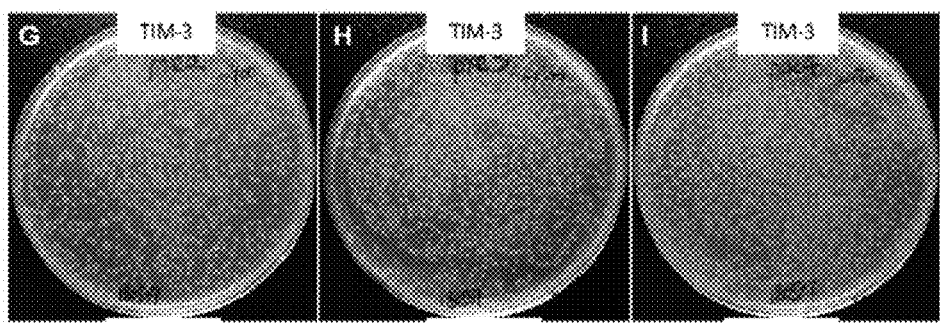

FIG. 18 is a schematic diagram of a colony count of resistance on a small test plate for connection of an embodiment.

Figure 19:
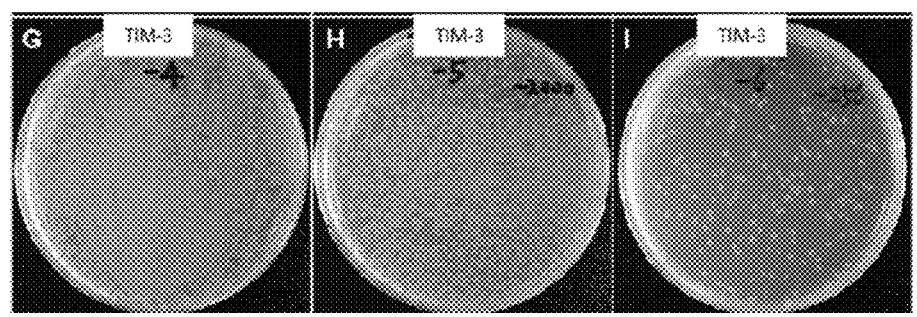

FIG. 19 is a schematic diagram of a library size determination of 4 VHH libraries of an embodiment.

Figure 20:
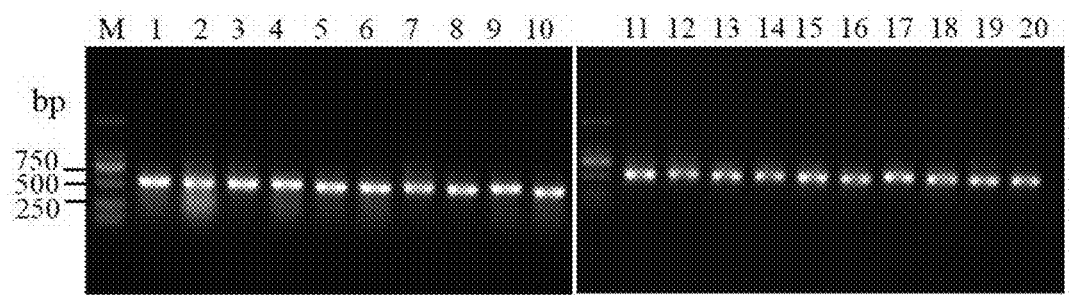

FIG. 20 is a schematic diagram of the agarose gel electrophoresis of the colonies of PCR products of an embodiment.

Figure 21:
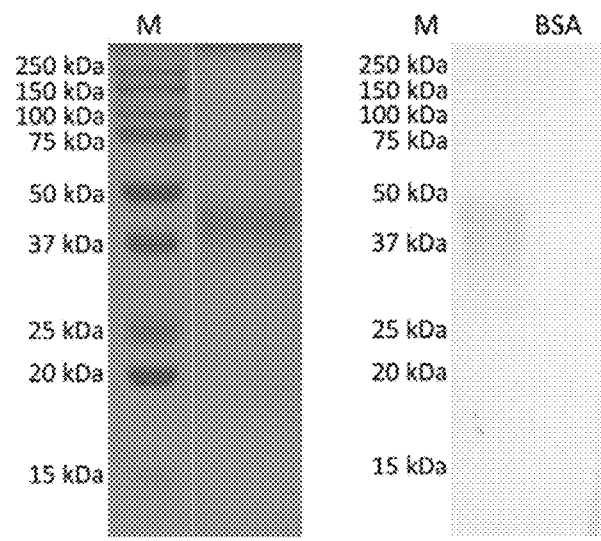

FIG. 21 is a schematic diagram of SDS-PAGE and Western-blot for detection of antigens of an embodiment.

Figure 22:
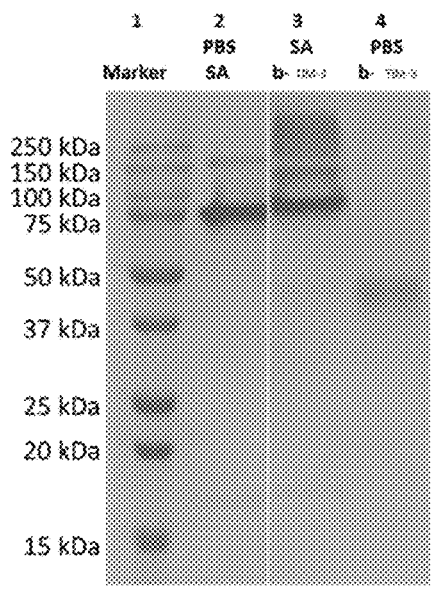

FIG. 22 is a schematic diagram of detection of biotin labeling efficiency of TIM-3 of an embodiment.

Figure 23:
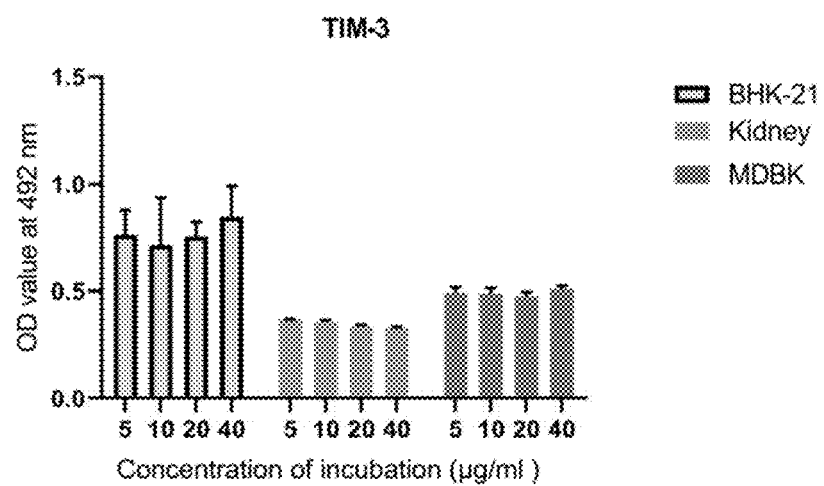

FIG. 23 is a schematic diagram of the cytotoxicity of the TIM-3 nanobody of an embodiment.

In the diagram: BHK-21: BHK-21 cell group; Kidney: kidney cell group of the sheep; MDBK: MDBK cell group. The data are expressed as mean±SD.

Figure 24:
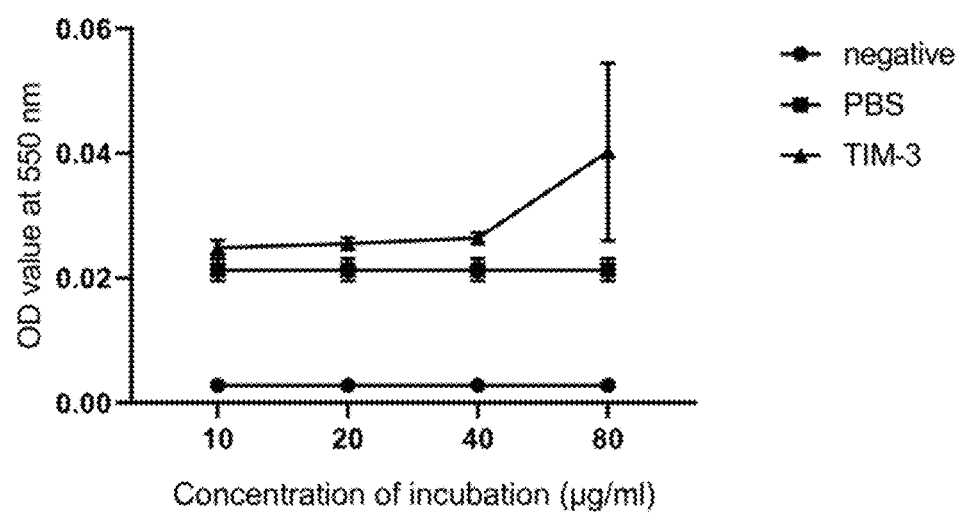

FIG. 24 is a schematic diagram of the effect of TIM-3 on the NO secretion level of immune cells of an embodiment.

In the diagram: negative: negative control group; PBS: PBS group; TIM-3: TIM-3 nanobody group.

DETAILED DESCRIPTION OF THE EMBODIMENTS

In order to make the purpose, technical scheme and advantages of the application more clear, the following embodiments are combined to further elaborate the application. It should be understood that the specific embodiment described herein is intended only to explain but not to define the application.

The existing monoclonal antibody has the following problems: heterology; the monoclonal antibodies are relatively large in volume, and has a long development cycle, high production cost and low output; the monoclonal antibody drugs are expensive in price, complicated in development and humanization, and limited in success rate; the existing monoclonal antibodies are difficult to produce on a large scale; the existing monoclonal antibodies are unstable, easy to degrade and thus leading to high conservation cost; easy to be polluted and maintenance cost thereof is high. The nanobody screened by the method of the application can bind to the target with high efficiency and specificity.

The principle of the application will be described in detail in combination with the attached drawings.

TIM-3 antigen of the application is expressed by transient transfection of mammalian cells, alpacas are used for immunized animals, biotinylation is used for screening, and the nanobody fragments obtained by the screening have their own unique gene sequences.

The nanobody in the embodiments is TIM-3 nanobody, the sequence thereof is SEQ ID NO:1.

Figure 1:
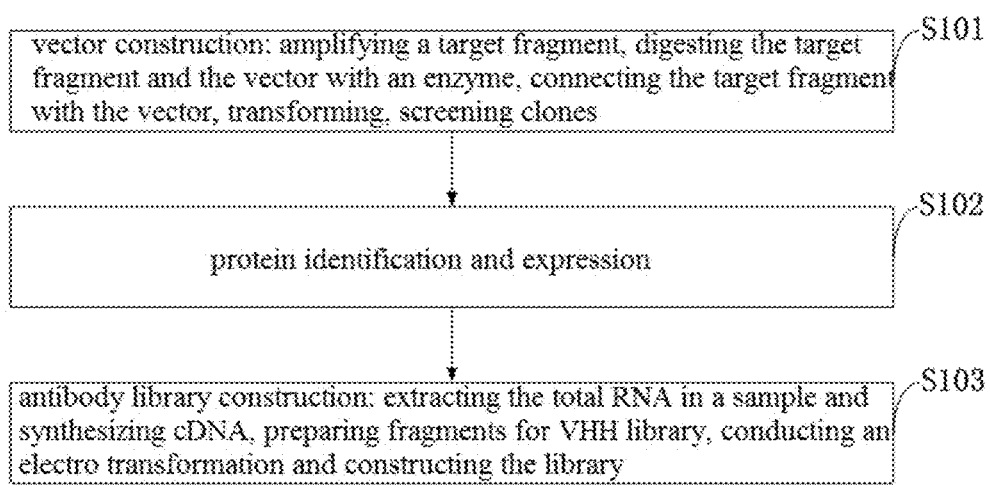
FIG. 1 is a flow chart of screening and identifying method for nanobody of an embodiment.

As shown in FIG. 1, the screening and identification methods for nanobodies in the embodiments of the application comprise the following steps:

S101: vector construction: amplifying a target fragment, digesting the target fragment and the vector with an enzyme, connecting the target fragment with the vector, transforming, screening clones;

S102: protein identification and expression;

S103: antibody library construction: extracting the total RNA in the a sample and synthesizing cDNA, preparing fragments for VHH library, conducting an electro transformation, and constructing the library.

In the preferred embodiments of the application, the amplifying the target fragment in S101 is specifically as follows:

(1) designing and synthesizing 2 primers, amplifying by PCR the sufficient target products; the primers sequences are:

```
TIM-3 upstream primer:
                          SEQ ID NO: 2
5'-GACACGAATTCGCCACCATGTTCAGCCACC-3', TIM-3 downstream primer:
                          SEQ ID NO: 3
5-GTGTCAAGCTTTCACTTGTCATCATCATCCTTGTA-3',
```

(2) the enzyme used in the PCR is Pfu high temperature polymerase.

In the preferred embodiments of the application, the amount of each ingredient in the PCR in S101 is as follows: primer concentration: 10D dissolved in 400 μl ddH$_2$O; reaction system: 50 μl; primer mix, (⅛) 0.4 μl×13.6, 8 μl in total; 10×pfu Buffer: 5 μl; each of the upstream primer and downstream primer: 2 μl; Pfu: 0.4 μl(5μ/μl); ddH$_2$O: replenishing water to 50 μl respectively.

The specific steps of the PCR amplification of the target fragment are as follows:

(1) the first round PCR procedure:

95° C. 3 min
95° C. 22 sec ⎫
50° C. 20 sec ⎬ 18 cyc.
72° C. 40 sec ⎭
72° C. 5 min The above is the first round PCR reaction system, the products of the first round PCR are used as the template prepared for the second round PCR.

(2) the second round PCR system:

The amount of each ingredient in the second round PCR is as follows: primer concentration: 10D dissolved in 400 μl ddH$_2$O; the upstream primer-1: 2 μl; the down stream primer-28: 2 μl; products of the first round procedure: 1 μl;

dNTP: 1 μl(25 mM each); 10× pfu Buffer: 5 μl; Pfu: 0.4 μl(5μ/μl); ddH$_2$O: replenishing water to 50 μl respectively;

(3) the second round PCR procedure:

95° C. 3 min
95° C. 22 sec ⎫
55° C. 20 sec ⎬ 22 cyc,
72° C. 45 sec ⎭
72° C. 5 min Conducting agarose gel electrophoresis for the products from the second PCR, collecting the purified fragments and preparing for digestion.

Digesting the PCR products by an enzyme.

The enzyme digestion system of the PCR fragment products is as follows: 50 μl in total; purified and collected fragments: 1 μg(20 μl); 10× FD Buffer: 5 μl; EcoRI: 1 μl(10μ/μl); HindIII: 1 μl(10μ/μl); ddH$_2$O: 23 μl; keeping the systems in a 37° C. thermostat water bath reacting for 2 h.

The enzyme digestion system of the vector is as follows: PCDNA3.1+: 1 μg; 10×FD Buffer: 5 μl; EcoRI: 1 μl(10μ/μl); HindIII: 1 μl(10μ/μl); ddH$_2$O: 42 μl; putting the system into a 37° C. thermostat water bath reacting for 2 h, collecting the enzyme digested vector and fragments.

Connecting the target fragments with the vector, i.e. connecting the collected and purified target DNA fragments with the vector; the connecting system is as follows: 20 μl in total; target fragments of the enzyme: 8 μl; digestion vector of PCDNA3.1+: 4 μl; 10×T4 DNA ligase Buffer: 2 μl, T4 DNA ligase: 1 μl(5μ/μl); ddH$_2$O: replenishing to 20 μl;

The operation of transforming, screening clones is specifically as follow: keeping the mixture for connecting in a 22° C. PCR Instrument for 1 h.

The principle of the application will be described further in combination with the specific embodiments.

EXAMPLE 1

The vector construction method in the embodiment was as follows:

1. The amplification of the target fragment was specifically as follows:

(1) two primers were designed and synthesized, and target products were amplified by PCR to be sufficient;

(2) the enzyme used in the PCR was Pfu high temperature polymerase.

The amount of each ingredient in the PCR was as follows: primer concentration: 10D dissolved in 400 μl ddH$_2$O; reaction system: 50 μl; primer mix, (⅛) 0.4 μl×13.6, 8 μl in total; 10×pfu Buffer: 5 μl; each of the upstream primer and downstream primer: 2 μl; Pfu: 0.4 μl(5μ/μl); ddH$_2$O:water was replenished to 50 μl respectively.

The specific steps of the PCR amplification of the target fragment were as follows:

(1) the first round PCR procedure:
95° C. 3 min

95° C. 3 min
95° C. 22 sec ⎫
50° C. 20 sec ⎬ 18 cyc.
72° C. 40 sec ⎭
72° C. 5 min The above was the first round PCR reaction system, the products of the first round PCR were used as the template prepared for the second round PCR.

(2) the second round PCR system:

The amount of each ingredient in the second round PCR was as follows: primer concentration: 10D dissolved in 400 µl ddH$_2$O; the upstream primer-1: 2 µl; the down stream primer-28: 2 µl; products of the first round procedure: 1 µl; dNTP: 1 µl(25 mM each); 10×pfu Buffer: 5 µl; Pfu: 0.4 µl(5µ/µl); ddH$_2$O:water was replenished to 50 µl respectively;

(3) the second round PCR procedure:

$$\left.\begin{array}{l}95° \text{ C. 3 min}\\ 95° \text{ C. 22 sec}\\ 55° \text{ C. 20 sec}\\ 72° \text{ C. 45 sec}\\ 72° \text{ C. 5 min}\end{array}\right\} 22 \text{ cyc.}$$

Figure 2:
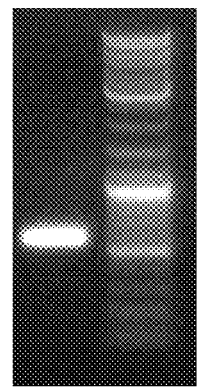
FIG. 2 is an original image of PCR agarose gel electrophoresis of an embodiment.

In the embodiment, as shown in FIG. 2, the original image of PCR agarose gel electrophoresis is the original image of the second round PCR agarose gel electrophoresis. The purified fragments was collected to prepare for digestion.

2. Digesting the above PCR products.

The enzymatic system of the PCR fragment products was as follows: 50 µl in total; purified and collected fragments: 1 µg(20 µl); 10×FD Buffer: 5 µl; EcoRI: 1 µl(10µ/µl); HindIII: 1 µl(10µ/µl); ddH$_2$O: 23 µl;
  the systems was kept in a 37° C. thermostat water bath reacting for 2 h.

Figure 3:
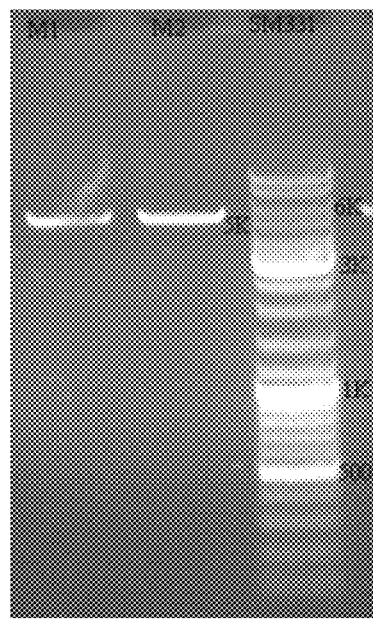
FIG. 3 is an agarose gel electrophoresis of the PCDNA3.1+ vector after digesting of an embodiment.

The enzyme digestion system of the vector was as follows: PCDNA3.1+: 1 µg; 10×FD Buffer: 5 µl; EcoRI: 1 µl(10µ/µl); HindIII: 1 µl(10µ/µl); ddH$_2$O: 42 µl;

In the embodiment, an agarose gel electrophoresis of the PCDNA3.1+ after digesting is shown in FIG. 3. The systems was kept in a 37° C. thermostat water bath reacting for 2 h, the digested vector and fragments were collected.

3. Connecting the target fragments with the vector.

The connecting system was as follows: 20 µl in total; target fragments of the enzyme: 8 µl; digestion vector PCDNA3.1+: 4 µl; 10×T4 DNA ligase Buffer:1 µl; T4 DNA ligase: 1 µl(5µ/µl); ddH$_2$O:water was replenished to 20 µl;

4. The operation of transforming, screening clones is specifically as follow: the mixture for connecting was kept in a 22° C. PCR Instrument for 1 h.

EXAMPLE 2

The specific steps of the nanobody library construction in the embodiment was as follows:

1) Experimental Design

The M13 phage display system was used to display the VHH antibody library, which was composed of pMECS phagemid vector, *E. coli* TG1 and M13KO7 helper phage. In the pMECS phagemid vector, the sequence before the Pst I restriction site is the coding sequence of the pelB secreting signal peptide and part of the amino acid in the first framework region of the antibody, pelB secreting signal peptide may guide the subsequent peptides to be secreted into the periplasmic cavity; the Not I restriction site is followed by the HA and 6×His labeled coding sequences for purification or detection of fusion proteins. The subsequential sequence codes the phage PIII capsid protein (as shown in FIG. 5). There is an amber termination codon between the 6×His label and gene III sequence, in the inhibited type strains(such as *E. coli* TG1), 10~20% of the amber termination codon might be translated into glutamic acid(Glu, or E), the fusion expression was conducted between VHH and gene III protein, after using the auxiliary phage M13KO7, the VHH antibody was shown at the end of the phage PIII protein N terminal.

The embodiment was shown in FIG. 5, which is a schematic diagram showing the sequence of the embodiment coding a phage PIII capsid protein.

Therefore, the total RNA of the sample was firstly extracted and reversely transcribed to cDNA, and then the camel antibody fragment was amplified by using the CAL-leader and CAL-CH2 primer pair. The ~600 bp band on the gel of the above PCR was cut and recovered and then was used as the template for subsequent PCR. VHH gene fragment was amplified by VHH-back and PMCF primer. The Not I restriction site was introduced into the 3'end of the VHH gene fragment (the 5' end of the VHH fragment contains the Pst I restriction site), and the fragment was inserted into the pMECS phagocyte vector by enzyme digestion and connection reaction, and then transformed into *E. coli* TG1 to construct the M13 single-stranded filamentous phage display camel nanobody immune library.

2) Experimental Material (1) Peripheral blood lymphocyte samples were collected from camel peripheral blood.

(2) cDNA synthesis, PCR amplification, restriction enzymes and T4 DNA ligase were purchased from Thermo Scientific and New England Biolabs.

(3) pMECS, *E. coli* TG1, Helper Phage M13KO7 and other experimental materials were reserved in Zoonosis laboratories.

Figure 4:
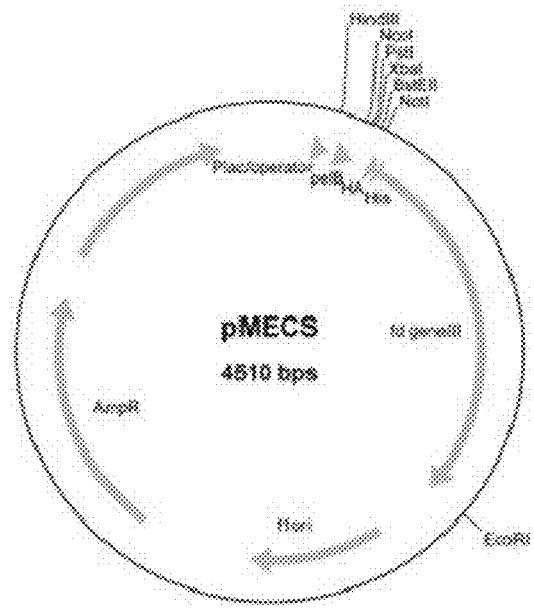
FIG. 4 is a pMECS plasmid map of the phagemid of an embodiment.

A pMECS plasmid map of the phagemid provided by the embodiment is shown in FIG. 4.

3) Experimental Result (1) Total RNA Extraction and cDNA Synthesis

The total RNA of the peripheral blood lymphocyte samples was extracted with Trizol reagent, and the quality of the total RNA was detected by agarose gel electrophoresis.

As shown in FIG. 6, it is a gel electrophoresis of total RNA sample. In the figure, the M refers to a DL2000 DNA marker.

The total RNA samples show very slight degradation, with 28S, 18S and 5S rRNA bands clearly visible, and the brightness of 28S bands was greater than 18S, indicating good RNA integrity.

The concentration of RNA samples was measured by Nanodrop, and the results showed that the concentration and purity of RNA samples met the requirements (Table 1). cDNA was synthesized by reverse transcription of 10 µg total RNA.

TABLE 1

| Concentration and purity of total RNA samples | | |
| --- | --- | --- |
| sample name | concentration (ng/µl) | $OD_{260}/OD_{280}$ |
| TIM-3 | 720.8 | 2.01 |

(2) Preparation of the Fragment for VHH Library

The camel antibody fragment was amplified by the CAL-leader and CAL-CH2 primers with the template of the above cDNA respectively, the PCR products were detected by 1% agarose gel electrophoresis, the results were shown in FIG. 3A: there are two bands in each samples, the molecular weight of main band is about 600 bp, moreover, there is a non-target band in the 900 bp site (the band should be traditional antibody fragments amplified). Sufficient amount of PCR products were conducted with electrophoretic, the 600 bp main band on the gel was cut and recovered as the template for subsequent PCR, and VHH was amplified with VHH-back and PMCF primers. The target band with the molecular weight consistent with the expectation (about 400 bp) was obtained by PCR amplification.

EXAMPLE 3

The protein identification and expression provided by the embodiment were as follows:
S1: Construction of the mammalian cell expression vector (plasmid template, His-Flag tag was added to the C end).
  1. vector plasmids containing target genes were amplified and extracted.
  2. the vector plasmid was subcloned to eukaryotic expression vector pcDNA3.1.
  3. the accuracy of plasmid construction was verified by sequencing.
  4. the recombinant plasmid pcDNA3.1 was obtained through moderate extraction.
S2: Mammalian cell culture, protein expression and small purification experiment.
  1. cell lines and materials
  cell line: HEK293 cell line.
  medium: DMEM (10% serum), DMEM (no serum).
  cultureware: 10 cm dish or 15 cm dish.
  2. HEK293 cell transfection (10 cm dish)
  (1) 24 h before transfection, the total amount of cells coated on the plate was $4\text{-}5\times10^6$/10 cm culture dish, and transfection was conducted when the cell growth condition was good and the density of adherent cells reached 50-80%.
  (2) 5 μg plasmid DNA to be transferred was added into the 1.5 mL centrifuge tube and mixed well.
  (3) 10 μl liposomes and the above DNA were added in sequence into 500 μl DMEM culture medium, mixed gently, and RT incubated for 30 min.
  (4) The liquid containing DNA and liposomes was carefully added to the culture dish, dispersed evenly, and cultured for 72 h in an incubator at 37° C., 5% $CO_2$.
  3. Observe and collect cells
  (1) after 72-hour transfection, the cell culture medium was removed carefully and the adherent cells were rinsed with precooling PBS once.
  (2) collect cell precipitation by centrifugation.
  4. Cell lysis
  (1) the added cell lysis buffer: Lysis Buffer: 50 mM Tris(pH8.0), 300 mM NaCl, 1% Triton X-100, 1 mM DTT, 5% glycerol.
  (2) 200 W ice bath ultrasound was conducted for 10 min.
  (3) the pyrolysis supernatant was collected at 16000 rpm×20 min at 4° C.
  5. Purification by Flag tag
  (1) flag filler and 1 ml column were used for purification.
  (2) the column was pre-balanced with a Binding Buffer (50 mM Tris(pH 8.0), 300 mM NaCl, 0.1% Triton X-100, 1 mM DTT, 5% glycerin) at 10 CV.
  (3) the lyses cell supernatant was added to the balanced column.
  (4) after finishing loading, the column was cleaned with Binding Buffer.
  (5) Wash Buffer (50 mM Tris(pH8.0), 500 mM NaCl, 1 mM DTT, 5% glycerin) was used to wash the column at 5-10 CV, and the non-specific adsorbed impurities were washed away.
  (6) Elution Buffer (50 mM Tris(pH8.0), 150 mM NaCl, 150 μg/μl Flag peptide, 1 mM DTT, 10% glycerol) was used to elute and collect the target protein.
  6. Western-blot detection
  (1) solution preparation:
  transfer buffer: 0.025M Tris Base, 0.192M glycine, 30% methanol 10×TBST: 250 mM Tris-Hcl (pH 8.0), 1.25M NaCl, 0.5% Tween20. Sealing solution: 1×TBST, 3% skim milk powder. Washing liquid: 1×TBST.
  (2) experimental procedure:
  A. membrane preparation: the PVDF membrane was cut into strips and soaked into methanol, shaked on the shaking table at room temperature for 1 min, added with 1×TBST after the methanol was removed.
  B. film transfer printing:
    i. SDS-PAGE electrophoresis.
    ii. the transfer to PVDF membrane was conducted with sandwich method.
    iii. sponge and filter paper were soaked in transfer buffer to pre-wet.
    iv. 300 mA transfer lasted for 80 min, sealed with sealing solution for 1 h at room temperature or 4° C. overnight.
  C. antibody detection:
    i. the primary anti-flag tag was diluted according to the instruction and incubated at 4° C. overnight.
    ii. washed with detergent for 3 times, 5 min each.
    iii. the secondary antibody was diluted with a blocking solution and incubated at room temperature for 1 h.
    iv. washed with detergent for 3 times, 5 min each.
    v. TMB color development detection.
S3: Protein identification result
  (1) Because the specific amino acid composition and arrangement of each protein is different, the SDS-PAGE gel thereof would present differently even for proteins with similar molecular weights. Protein molecular marker is a reference of molecular weight, in SDS-PAGE electrophoresis, the target protein may be completely consistent with the theoretical molecular weight, or it may be higher or lower.
  (2) The molecular weight of secretory protein samples modified by glycosylation is higher than that of theoretical ones. In addition, the process of glycosylation of proteins is not completely homogeneous, and it is often appeared that the protein bands dispersed in target protein, multiple bands close to each other, which are typical electrophoresis manifestations of secreted proteins.

The application will be further described in combination with experiments.

Experiment1:
S1: Experiment: Protein Expression and Immunity of Alpacas

TIM-3 extracellular domain sequence was amplified by PCR, and recombinant pcDNA3.1 plasmid was constructed. The plasmid was transfected into HEK293 cell line to express the target protein, and the target protein was detected by SDS-PAGE and Western-blot. The results showed that the target band was successfully amplified by PCR, and the enzyme digestion was shown successful by 1% agarose gel electrophoresis. 10% SDS-PAGE showed successful expression of the target protein. Western-blot analysis confirmed the specificity of the protein.

1. Materials
1.1 Plasmids and Strains pcDNA3.1 plasmid, HEK293 cells and HEK293 competent cells were all stored in the laboratory jointly built by Xinjiang ethnic group and the provincial department of high incidence.

1.2 Main Biochemical Reagent

Fetal bovine serum, DMEM medium, purchased from Gibco.

EcoR I endonuclease, Hind III endonuclease, rat His monoclonal IgG antibody resistance, horseradish peroxidase (HRP) labeled rabbit anti rat IgG, purchased from sangon biological engineering (Shanghai) co., LTD.

Nickel column, purchased from GE.

TMB color development solution, purchased from Beijing Zhongshan Jinqiao Biotechnology Co., LTD.

SM331 GeneRuler DNA Ladder Mix, purchased from Thermo Scientific.

(The rest of the reagents were produced by Sangon Company).

The enzymes used were NdeI, XhoI and corresponding FDBuffer produced by Thermo Scientific Company.

Electrophoresis instrument were DYY85 of Beijing Liuyi instrument Factory.

PCR product purification was performed using a PCR purification kit made by Sangon Company.

The ligase used in 10× T4 DNA ligase Buffer was produced by Thermo Scientific.

2. Method

Preparation of the TIM-3 Immunogen

Primers designed for Primer Premier 5.0 software were obtained from Uniprot database and synthesized by Sangon Bioengineering (Shanghai) Co., LTD.

It was synthesized by Sangon Bioengineering (Shanghai) Co., LTD, and the synthesized fragment was used as PCR template.

| Primer name | Primer sequence |
|---|---|
| TIM-3 upstream primer | 5'-GACACGAATTCGCCACCATGTTCAGCCACC-3' |
| TIM-3 downstream primer | 5'-GTGTCAAGCTTTCACTTGTCATCATCATCCTTGTA-3' |

The amount of each ingredient (primer concentration: 1OD dissolved m 400 μl ddH$_2$O)

TABLE 2

| PCR system | |
|---|---|
| ingredients | volume |
| upstream primer | 2 μl |
| downstream primer | 2 μl |
| target gene | 3 μl |
| dNTP | 1 μl(25 mM each) |
| 10× pfu Buffer | 5 μl |
| Pfu | 0.4 μl(5μ/μl) |
| ddH$_2$O | add up to50 μl |

PCR Procedure of the TIM-3 Target Fragment:

TABLE 3

| PCR procedure | | |
|---|---|---|
| temperature | time | |
| 95° C. | 3 min | |
| 95° C. | 22 sec | |
| 55° C. | 20 sec | 22 cyc |
| 72° C. | 45 sec | |
| 72° C. | 5 min | |

The 1% agarose gel electrophoresis was conducted after PCR, and the purified enzyme fragment was collected for preparation.

Restriction Enzyme Digestion and Identification

Restriction enzyme digestion was conducted to the PCR products, the restriction enzyme digestion system for the PCR product fragments was 50 μl in total.

TABLE 4

| enzyme digestion system for PCR product fragments 50 μl | |
|---|---|
| ingredients | volume |
| collected and purified fragments | 1 μg(20 μl) |
| 10× FD Buffer | 5 μl |
| EcoRI | 1 μl(10μ/μl) |
| HindIII | 1 μl(10μ/μl) |
| ddH$_2$O | 23 μl |

The systems was kept in a 37° C. thermostat water bath reacting for 2 h.

Restriction Enzyme System of the Vector:

TABLE 5

| restriction enzyme system of the vector | |
|---|---|
| ingredients | volume |
| PCDNA3.1+ | 1 μg |
| 10× FD Buffer | 5 μl |
| EcoRI | 1 μl(10μ/μl) |
| HindIII | 1 μl(10μ/μl) |
| ddH$_2$O | 42 μl |

The systems was kept in a 37° C. thermostat water bath reacting for 2 h, and the digested vector and fragments were collected.

The collected and purified target DNA fragment was connected with vector:

TABLE 6

| Connecting system: 20 μl | |
|---|---|
| target fragment of restriction enzyme | 8 μl |
| digestion vector PCDNA3.1+ | 4 μl |
| 10X T4 DNAligase Buffer | 2 μl |
| T4 DNAligase | 1 μl (5 μ/μl) |
| ddH$_2$O | add up to 20 μl |

The connecting mixture was kept in the PCR instrument at 22° C. for 1 h. The above solution was transferred into HEK293 competent cells by heat shock method at 42° C. The positive clones were detected and the recombinant plasmid was extracted.

SDS-PAGE Detection:
HEK293 cells were coated on the medium 24 h before transfection, and transfected when the cell growth condition was good and the density of adherent cells reached 50%~80%. 10 μL liposomes were added to the 500 μL DMEM medium, 5 μg recombinant plasmid was added, gently mixed, and incubated at constant temperature for 30 min. The liquid containing DNA and liposomes was carefully added to the culture dish, dispersed evenly, and cultured for 72 h in an incubator at 37° C. and 5% $CO_2$. The culture medium was removed, the cells were collected centrifugally, the cell lysis buffer was added, and the ultrasound was performed in an ice bath of 200 W for 10 min. Centrifugation was at 16 000 r/min for 20 min. The lysed supernatant was collected for 10% SDS-PAGE electrophoresis. The protein was purified by nickel column after expression.

Specific Western-Blot Detection:
PVDF membrane was cut into strips and soaked in methanol. The membrane was cultured in a shaking table for 1 min at room temperature. After the methanol was removed, 1×TBST was added for SDS-PAGE electrophoresis, and the protein was electrotransferred to PVDF membrane by the sandwich method. The filter paper was soaked in transfer buffer to pre-wet, and a 300 mA transfer was lasted for 80 min. It was sealed with a blocking buffer at room temperature for 1 h. The primary antibody was diluted to 3000 fold, incubated at 4° C. overnight, and washed with PBST for 3 times, 5 min each. The secondary antibody was diluted to 5000 fold with a blocking buffer and incubated at room temperature for 1 h, and washed with PBST for 3 times, 5 min each, and TMB solution was used for color development. TIM3 primary antibody was anti-TIM3 antibody (F38-2E2) (Mouse monoclonal antibody F38-2E2 to TIM3, Anti-TIM3 Antibody (F38-2E2) ab104709), and the secondary antibody was goat polyclonal antibody to Mouse IgG-H&L (HRP) antibody (abcam Company ab6789). Method was the same as above.

In the primary immunization, 0.5 ml freund's complete adjuvant and 0.5 ml protein were emulsified for subcutaneous and intradermal immunization;

0.25 ml freund's complete adjuvant and 0.25 ml protein was emulsified, and the alpaca was immunized subcutaneously respectively at 28 days (2nd immune), 49 days (3rd immune), and 70 days (4th immune);

0.125 ml freund's complete adjuvant and 0.125 ml protein was emulsified, and the alpaca was immunized subcutaneously respectively at 91 days (5th immune), 112 days (6th immune); at day 122, the lymphocyte was isolated.

TABLE 8

| blood sampling time | |
|---|---|
| 0 day | 7 days |
| 28 days | 35 days |
| 49 days | 56 days |
| 70 days | 77 days |
| 91 days | 98 days |
| 112 days | 119 days |
| 133 days | 140 days |

ELISA Test Procedure:
The plate was coated at 4° C. overnight with an antigen 200 ng/well. The plate was washed with PBST (0.1%) once, and sealed at 37° C. for 2 h with 1×bloker 300 μl/well. The plate was washed with PBST (0.1%) once, and 0.5×blocker gradient dilution antiserum was added at 100 μl/well, keeping 37° C. for 1 h. The plate was washed with PBST (0.1%) for 3 times, anti-alpaca secondary antibody was diluted with 0.5×blocker to 1:15,000 and added to the plate at 37° C. and kept for 1 h. The plate was washed with PBST (0.1%) for 3 times, washed with PBS for 3 times, and color developed with TMB 100 μl/well for about 20 min, and the development was terminated with 2M $H_2SO4$ 50l/well. The reading of OD450-OD630 nm on the microplate reader was obtained.

Lymphocyte Separation:
The lymphocyte separation solution was preheated to 22° C. 200 ml of peripheral blood was collected from each alpaca using heparin sodium anticoagulant tubes. The hole blood was diluted with an isometric tissue diluent. An equal volume separation solution was added to the centrifuge tube and then centrifuged at room temperature with the horizontal rotor 1000 g for 30 min. The buffy coats was sucked and 10 ml PBS washing solution was added to wash the buffy coats cells. The samples were centrifuged at 250 g for 10 min. The supernatant was discarded, the cells were resuspended with 5 ml PBS, and centrifuged at 250 g for 10 min. The supernatant was discarded, the cells were resuspended with 5 ml PBS, and centrifuged at 250 g for 10 min. The supernatant was discarded, and the cells were resuspended with Trizol.

S2: Construction of Camel Nanobody Immune Library
Total RNA was extracted from camel peripheral blood lymphocytes and reversely converted to cDNA. The fragments for VHH library were amplified by using camel antibody primers. Four kinds of VHH library fragments were respectively inserted into pMECS phagemid vector and transformed into E. coli TG1, to construct phage display antibody immune library, the library size was larger than $10^9$ CFU. Twenty clones were randomly selected from the

TABLE 7

| | immunization protocol | | | | | | |
|---|---|---|---|---|---|---|---|
| item | primary immune | 2nd immune | 3rd immune | 4th immune | 5th immune | 6th immune | separate lymphocyte |
| immune time | 0 day | 28 days | 49 days | 70 days | 91 days | 112 days | 122 days TIM-3 |
| Immunizing dose adjuvant | 1 ml freund's complete adjuvant | | 0.5 ml fia | | 0.25 ml | | |
| Immunization ways | subcutaneous, intradermal | | subcutaneous | | | | | library for sequencing and analysis to ensure that more than 99% of the clones in the library contained the target insertion sequence.

1. Experimental Materials

Kits such as for cDNA synthesis, PCR amplification, and tool enzymes such as restriction enzymes and T4 DNA ligase were purchased from Thermo Scientific and New England Biolabs. PMECS, *E. coli* TG1, Helper Phage M13KO7 and other experimental materials were from the laboratory.

2. Experimental Method

Total RNA Extraction and cDNA Synthesis

Trizol was used to extract total RNA from the camel peripheral blood lymphocytes and the quality of total RNA was detected by agarose gel electrophoresis.

Preparation of Fragments for VHH Library cDNA was used as template, camel antibody fragments were amplified with primers CAL-leader and CAL-CH2, and appropriate amount of PCR products were taken to conduct 1% agarose gel electrophoresis detection.

```
Sequence of primer CAL-leader:
GTCCTGGCTGCTCTTCTACAAGG

Sequence of primer CAL-CH2:
GGTACGTGCTGTTGAACTGTTCC
```

PCR System:

Pfu high fidelity DNA polymerase was used (TransStart FastPfu DNA Polymerase, AP221-01).

| Component | Volume | Final Concentration |
|---|---|---|
| 5 × pfu Buffer | 10 µl | 1× |
| dNTPs (2.5 mM each) | 4 µl | 0.2 mM |
| CAL-leader(10 µM) | 1 µl | 0.2 µM |
| CAL-CH2(10 µM) | 1 µl | 0.2 µM |
| cDNA | 2 µl | |
| pfu DNA polymerase | 1 µl | 2.5 units |
| ddH2O | 31 µl | |

PCR Procedure

| Number of cycles | Temperature | Time |
|---|---|---|
| 1 cycle | 95° C. | 2 min |
| 30 cycles | 95° C. | 30 s |
| | 56° C. | 30 s |
| | 72° C. | 1 min |
| 1 cycle | 72° C. | 5 min |
| 1 cycle | 4° C. | ∞ |

Connection and Transformation Pre-Experiments

Before the formal construction of the library, the mass of phagemid vector, the connection efficiency of vector and VHH library fragments were tested and evaluated through connection and transformation pre-experiments. T4 DNA Ligase was used to ligate the VHH fragments and the phagemid vector both of which were digested by Pst I/Not I at a different ratio (the same amount of vector was used in each group), then *E. coli* TG1 chemosensitizer cells were transformed, and the coated plate containing ampicillin containing Amp resistant was applied for colony counting.

The sample had two bands, a main band with the molecular weight of about 600 bp, and a non-target band at 900 bp, which could be the amplified fragment of traditional antibody. Electrophoresis was conducted on sufficient amount of PCR products, and the main band of 600 bp was cut from the gel and recovered as the template for subsequent PCR. VHH was amplified by VHH-back and PMCF primers, and the target band of about 400 bp in molecular weight was obtained by PCR amplification as expected.

```
Sequence of VHH-back primer:
GATGTGCAGCTGCAGGAGTCTGGRGGAGG

Sequence of PMCF primer:
CTAGTGCGGCCGCTGAGGAGACGGTGACCTGGGT
```

PCR System

| Component | Volume | Final Concentration |
|---|---|---|
| 5 × pfu Buffer | 10 µl | 1× |
| dNTPs (2.5 mM each) | 4 µl | 0.2 mM |
| PMCF (10 µM) | 1 µl | 0.2 µM |
| VHH-back (10 µM) | 1 µl | 0.2 µM |
| template | X µl | 50 ng/50 µl system |
| pfu DNA polymerase | 1 µl | 2.5 units |
| ddH2O | add to 50 µl | |

PCR Procedure

| Number of cycles | Temperature | Time |
|---|---|---|
| 1 cycle | 95° C. | 2 min |
| 25 cycles | 95° C. | 30 s |
| | 58° C. | 30 s |
| | 72° C. | 1 min |
| 1 cycle | 72° C. | 5 min |
| 1 cycle | 4° C. | ∞ |

Electro Transformation and Library Construction

In the connection experiment of the formal library construction, the vector was connected to four kinds of VHH fragments at the optimal ration determined from the connection and transformation pre-experiment. The purified ligand was electrically transformed into *E. coli* TG1, and 15 ml of the transformed product was obtained.

10 µl (i.e. 102 ml) was used for a series of tenfold gradient dilutions, and three gradients of $10^{-4}$, $10^{-5}$ and $10^{-6}$ were used for ampicillin resistance plate counting to evaluate library size, whose computational formula was as follows: library size=clone numbers×dilution times×total volume of transformed products (ml). All the remaining transformed products were coated to 15 plates with a diameter of 15 cm containing Amp resistant and cultured overnight. The next day, after scraping and mixing, glycerin with a final concentration of 20% was added, the final products were divided and frozen at −80° C.

Protocol of Electro Transformation:

1) preparing *E. coli* TG1 electrically transformed competent cells.
2) adding an appropriate amount of the purified ligand into TG1 competent cells, mixing them evenly, and dividing them into 0.2 cm electro transformation cups.
3) using the electro transformation instrument for electro transformation, BIORAD recommended transformation conditions: 2.5 kV, 25 µF, 200Ω.

4) adding 2YT culture medium to the electro transformation cups, resuspending the competent cells, and recovering the cells at 37° C., 150 rpm for 30 min.

Quality Analysis of Immune Library

Twenty monoclones were randomly selected from gradient dilution plates of each library, and colony PCR was performed using primer MP57 and PMCF. These clones were sequenced by using primer MP57 (-TTATGCTTCCGGCTCGTATG-).

PCR System:

| Component | Volume | Final Concentration |
|---|---|---|
| 2 × Taq Plus MasterMix | 25 μl | 1× |
| MP57 (10 μM) | 2 μl | 0.4 μM |
| PMCF (10 μM) | 2 μl | 0.4 μM |
| Template | 1 μl | |
| ddH$_2$O | 20 μl | |

PCR Procedure

| Number of cycles | Temperature | Time |
|---|---|---|
| 1 cycle | 94° C. | 2 min |
| 27 cycles | 94° C. | 30 s |
| | 57° C. | 30 s |
| | 72° C. | 1 min |
| 1 cycle | 72° C. | 2 min |
| 1 cycle | 4° C. | ∞ |

3. Result 3.1 PCR Amplification

It was indicated that the target band was successfully amplified by PCR with the target band clear and consistent with the expected size by 1% agarose gel electrophoresis. FIG. 7 is a schematic diagram of PD-1 PCR amplification results provided by an embodiment of the application; In the diagram: M.DL-10 000 Marker; 1. target band. FIG. 8 is a schematic diagram of PD-L1 PCR amplification results provided by an embodiment of the application; In the diagram: M.DL-10 000 Marker; 1. target band. FIG. 9 is a schematic diagram of TIM-3 PCR amplification results provided by an embodiment of the application; In the diagram: M.DL-10 000 Marker; 1. target band. FIG. 10 is a schematic diagram of CTLA-4 PCR amplification results provided by an embodiment of the application; In the diagram: M.DL-10 000 Marker; 1. target band. FIG. 11 is a schematic diagram of the results of enzyme digestion identification provided by an embodiment of the application; In the diagram: 1,2. pcDNA3.1 enzyme digested bands; M.DL–10 000 Marker.

3.2 Enzyme Digestion Identification

After pcDNA3.1 plasmid was digested by enzyme, 1% agarose gel electrophoresis was used to detect the bands with the size of 5,300 bp (FIG. 10), which was consistent with the expected size, indicating that the enzyme digestion of recovered fragments was successful. The recovered enzyme digestion vectors and fragments were verified by gel electrophoresis. The target fragment was extracted with plasmid extract kit.

TIM-3 enzyme digestion identification was shown in FIG. 12.

3.3 SDS-PAGE Detection

The detection results of TIM-3 SDS-PAGE were shown in FIG. 13.

The cell culture was analyzed by 10% SDS-PAGE gel electrophoresis, which showed that the target band appeared at ku site, which was consistent with the expected size, indicating that the protein was successfully expressed and that the protein was expressed in a soluble form.

Specific Western-blot detection was shown in FIG. 14.

The immunization results of alpaca were shown in Table 16

TABLE 9

| | 12800 fold | 25600 fold | 51200 fold | 102400 fold | 204800 fold | 409600 fold | PBS |
|---|---|---|---|---|---|---|---|
| TIM-3 preimmune | 0.107 | 0.075 | 0.055 | 0.045 | / | / | 0.042 |
| TIM-3 the 6th immune | OUT | OUT | OUT | 1.813 | 0.983 | 0.47 | 0.04 |

Construction of the Phage Library

Total RNA Extraction and cDNA Synthesis

As shown in FIG. 15, the four total RNA samples showed very slight degradation, with 28S, 18S and 5S rRNA bands clearly visible, and the brightness of 28S bands was greater than that of 18S, indicating good RNA integrity.

The concentration of RNA samples was measured by Nanodrop, and the results showed that the concentration and purity of RNA sample met the requirements (Table 17).

TABLE 10 concentration and purification of the total RNA

| Sample name | concentration (ng/μl) | OD$_{260}$/OD$_{280}$ |
|---|---|---|
| TIM-3 | 720.8 | 2.01 |

Construction of the VHH Library Fragments

The results were shown in FIG. 16-A: each of the four samples had two bands, the main band with the molecular weight about 600 bp and a non-target band at 900 bp (this band could be an amplified fragment of the traditional antibody).

Electrophoresis were conducted on sufficient amount of PCR products, the 600 bp main band was cut and recovered as the template for subsequent PCR, and VHH was amplified with VHH-back and PMCF primers. The results were shown in FIG. 16-B: target bands with molecular weight consistent with the expected size (about 400 bp) were obtained by PCR amplification.

The results were shown in FIGS. 17 and 18: Pre-test 1: no insert fragments, i.e. the vector was self-connected, showing nine colonies. Vector and VHH gene fragment are connected and transformed to *E. coli* TG1 at different ratios, and the bacterial colony growth on ampicillin resistant plate was observed. After being transformed, 1 ml culture medium was added to the resistant plate for recovery, and 100 μl colonies were coated on the plate for culture and counting. Therefore, the number of clones on the plate was one-tenth of the actual number.

Electro Transformation and Library Construction

As shown in FIG. 19: the number of clones in the gradient of TIM-3 library -5 and -6 was ~2000 and 256 respectively, so the library size was: $[256 \times 15 \times 10^6 + (2000+256) \times 15 \times 10^5] \div 2 = 3.6 \times 10^9$.

Quality Analysis of Immune Library

As shown in FIG. 20, all the clones had a specific band with a molecular weight of about 500 bp, indicating that all the clones were positive. These clones were sequenced by using primer MP57 (TTATGCTTCCGGCTCGTATG).

S3: Screening of the Nanobody

1. Experimental Materials

The plate pre-coated with the NeutrAvidin, Dynabeads and reagents were mainly purchased from Thermo Scientific, Sinopretics and other companies. Experimental materials such as Helper Phage and *E. coli* TG1 are from the laboratory.

2. Experimental Method

The antiserum titer of TIM-3 was detected by gradient dilution ELISA method before and after TIM-3 immunization. After TIM-3 coating (200 ng/well), the antiserum was added with gradient dilution. The secondary antibody used was anti-allama-HRP with 1:15000 dilution, and finally the color was developed with TMB substrate.

SDS-PAGE, Western-blot and biotin-labeling could be used in TIM-3 protein samples testing. The loading amount of sample was 2 μg for SDS-PAGE. Western-blot analysis was performed with 1:20000 dilution of antiserum and 1:2000 working concentration of anti-alpaca-HRP secondary antibody. The color was developed by chemiluminescence method, the same as above.

Biotin labeling and efficiency detection of the target TIM-3: biotin labeling was performed on TIM-3 under the condition of 0.25 mg/ml (TIM-3), pH 7.4, protein to biotin ratio of 1:15, and 1 h at room temperature. The labeled protein was desalted with PD-Midi desalination column to remove dissociated biotin, and the buffer was PBS 5% glycerol (pH7.4), and finally, the protein was respectively stored at −70° C. after separating. In order to detect the biotin-labeling efficiency of TIM-3, 5 μg streptavidin (SA) and 5 μl PBS were respectively added to two 1.5 μg labeled copies of b-TIM-3. In addition, 5 μg SA was also taken and added with 5 μl PBS as SA sample control. After the reaction at room temperature for 1 h, 5 μl non-reductive loading buffer was respectively added, and SDS-PAGE was performed directly without heating to denature.

In vitro directed screening was performed, and three rounds of screening were conducted for TIM-3 with the constructed immune library.

Identification

1) Monoclonal Phage ELISA Analysis 322 clones from the second and third round elution enrichment were selected for verification of Monoclonal phage ELISA, coated with TIM-3 and BSA (as a control)200 ng/well.

2) Soluble ELISA Analysis

The clone specific to TIM-3 sequence (in *E. coli* TG1) was induced by IPTG at 30° C., and then the bacteria were collected after centrifugation for periplasmic cavity extraction. The periplasmic cavity extracted samples were diluted ten fold with 0.5×blocker and added into TIM-3 and BSA both of which were coated and sealed, while TG1 (without phagemid) periplasmic cavity extracts were used as negative controls. Mouse anti-HA tag monoclonal antibody (ProteinTech, 1:5000 dilution) was used as a secondary antibody and sheep anti-mouse HRP (1:500 dilution) was used as a tertiary antibody to detect the activity of soluble nanobody expression.

The expression and purification of the construction of the pET28a-SUMO vector was to improve the expression and activity of nanobody, 11 viable TIM-3 nanobody clones were constructed into pET28a-SUMO vector for intracellular expression, and purified with Ni column after ultrasonic destruction.

The purified nanobody was gradient diluted with 0.5× Blocker and added to TIM-3 and BSA (200 ng/well) both of which were coated and sealed, and PBS was used as negative control. Mouse anti-HA tag monoclonal antibody (ProteinTech, 1:5000 dilution) was used as a secondary antibody and sheep anti-mouse HRP (1:500 dilution) was used as a tertiary antibody to detect the activity of soluble nanobody expression.

3. Experimental Result

The antiserum titer detect result of TIM-3 project was high, reaching 1:24800.

TABLE 11

Detection on serum titer of alpaca before and after immunization

| Antiserum dilution ratio | Serum after immune | Serum before immune |
|---|---|---|
| 200 | / | 0.76 |
| 400 | OUT | 0.725 |
| 800 | OUT | 0.547 |
| 1600 | OUT | 0.35 |
| 3200 | OUT | 0.232 |
| 6400 | OUT | 0.163 |
| 12800 | OUT | 0.107 |
| 25600 | OUT | 0.075 |
| 51200 | OUT | 0.055 |
| 102400 | 1.813 | 0.045 |
| 204800 | 0.983 | / |
| 409600 | 0.47 | / |
| PBS | 0.04 | 0.042 |

OUT represents that ELISA value greater than 3 at OD450 nm.

SDS-PAGE, Western-blot and biotin labeling of TIM-3 protein samples

1) Screening Antigen for SDS-PAGE and Western-Blot Detection:

As shown in FIG. 21, TIM-3 was detected by SDS-PAGE, and the results show that the protein is of high purity, non-degradation, and the molecular weight is about 45 kDa, which meet the requirements of subsequent labeling and screening. Western-blot results showed specific antiserum identification of TIM-3.

2) Detection of TIM-3 Biotin Labeling Efficiency

The detection results of biotin labeling efficiency was shown in FIG. 22. The figure shows that the SA+b-TIM-3 lane has an significant band migration compared with the SA+PBS lane, and the b-TIM-3 bands near 45 kDa are significantly reduced compared with the equivalent b-TIM-3+PBS group, with almost no protein residue, and therefore the labeling efficiency is estimated to be >90%.

In Vitro Directional Screening

Three rounds of screening were conducted for b-TIM-3 with the constructed immune library. The schemes and results were shown in the following table:

TABLE 12

| Round | Conditions | Input | Output | Enriching factor |
|---|---|---|---|---|
| 1st-P | Target protein: b-TIM-3 (10 µg)<br>Blocking: 2% Milk-PBS<br>Washing: 0.1% Tween20-PBS, 10 times<br>Elution: 0.2M Glycine-HCl, pH 2.2<br>Pre-counter select: None | $1.0 \times 10^{13}$ | $1.3 \times 10^{7}$ | $7.7 \times 10^{5}$ |
| 2nd-P | Target protein: b-TIM-3 (5 µg)<br>Blocking: 2% Milk-PBS<br>Washing: 0.2% Tween20-PBS, 15 times<br>Elution: 0.2M Glycine-HCl, pH 2.2<br>Pre-counter select: None | $1.3 \times 10^{12}$ | $2.0 \times 10^{8}$ | $6.5 \times 10^{3}$ |
| 3rd-P | Target protein: b-TIM-3 (1 µg)<br>Blocking: 2% Milk-PBS<br>Washing: 0.2% Tween20-PBS, 20 times<br>Elution: 0.2M Glycine-HCl, pH 2.2<br>Pre-counter select: None | $8.6 \times 10^{11}$ | $4.8 \times 10^{8}$ | $1.8 \times 10^{3}$ |

The results show that there is significant enrichment in the screening of the second round and a certain degree enrichment in the third round.

Identification

1) Monoclonal Phage ELISA Analysis

ELISA test results annex (TIM-3 monoclonal phage ELISA summarizing), the positive rate was about 80%, 51 strong positive clones were selected for sequencing, the result showed there was 23 sequence-specific clones in total.

2) Soluble ELISA Analysis

The results were shown in Table 18, a total of 11 nanobodies could be soluble and of good activity. Clones with the same background color marker had high sequence similarity.

TABLE 13

| Serial number | TIM-3 (200 ng/well) | BSA (200 ng/well) |
|---|---|---|
| CM03-7 | 0.385 | 0.047 |
| E. coli TG1 | 0.039 | 0.044 |

In combination with the specific detection test, the following was to detect the screened nanobodies:

1. Method 1.1 Nanobody Cytotoxicity Experiment

BHK-21 cells, MDBK cells and kidney cells of sheep were recovered with 37° C. warm water. Cell culture medium (90% DMEM+10% FBS) was added and the cells were subcultured on 96-well plates with $6 \times 10^{3}$ cells per well, allowing for the cell attachment and incubating for 3 hours, TIM-3 nanobodies were added. The final concentration gradient was set as: 5 µg/ml, 10 µg/ml, 20 µg/ml, and 40 µg/ml, 4 in total. 20 µl/well MTS reagent was added to each well and incubated at 37° C. for 3 hours. The absorbance was measured at 492 nm after oscillation.

1.2 NO Detection Experiment of Nanobody and Phage

Mouse immune cells were added to a 96-well plate for 3 h and then T7 phage was added with a final concentration of 1 µg/ml, and sequently followed by incubation for 24 h. TIM-3 nanobody was diluted with culture medium (90% DMEM+10% FBS) and added into the wells. The final concentration was adjusted to that of 10 µg/ml, 20 µg/ml, 40 µg/ml, and 80 µg/ml, with three replicates per sample. Cells were cultured in the cell incubator for 38 h. In the control group, 100 µl of the extracting solution, 50 µl of reagent I and 50 µl of reagent II were added(reagent I and reagent II were the reagents in the NO detection kit purchased from Beijing Solarbio Biotechnology Co., Ltd.). In the test group, 100 µl of the sample, 50 µl of reagent I and 50 µl of reagent II were added. The solutions were mixed well and stood at room temperature for 15 min to determine the absorbance value at 550 nm.

1.3 Data Analysis

The results were expressed as mean±standard deviation (SD).

Statistical analysis was performed by using GraphPad Prism 8 software, and significant differences were analyzed by Mann-Whitney U test (*=P<0.05, **=P<0.01).

1.4 Changes of IL-4, IFN-γ cytokines and NO secretion in mice after being injected with nanobody BalB/C mice were injected with antibodies of 0.1 mg each. Each injection was 0.2 ml with a concentration of 0.5 mg/ml. The groups were for example as follows: there were two PBS control groups, which were not duplicates or mistakes but intently divided into two groups to correspond to *Staphylococcus aureus* and *Streptococcus agalactiae* which were subsequently used in protective tests.

| Antibody group injection | |
|---|---|
| PBS control | 8 mice |
| TIM-3 | 8 mice |
| PBS control | 8 mice |
| TIM-3 | 8 mice |

Three days after immunization, blood was collected and serum was separated to detect the levels of cytokines IL-4, IFN-γ and NO (IL-4 detection kit, IFN-detection kit and NO level detection kit were purchased from Beijing Solarbio Biotechnology Co., LTD.).

1.5 Protective Tests of *Staphylococcus aureus* and *Streptococcus agalactiae*

*Staphylococcus aureus* and *Lactococcus agalactis* were injected separately, wherein *Staphylococcus aureus* was injected with 150 µl/$1.9 \times 10^{9}$ cfu (the lowest lethal dose in mice determined by multiple studies). *Lactococcus agalactis* was injected with 200 µl//$5.1 \times 10^{10}$ cfu (the lowest lethal dose in mice determined by multiple studies).

The mice were observed and recorded 24 hours later.

2. Result 2.1 Nanobody Cytotoxicity Detection

The cytotoxicity of TIM-3 nanobody was shown in FIG. 23. In FIG. 23, BHK-21 refers to BHK-21 cell group; Kidney refers to Sheep Kidney cells; MDBK refers to MDBK cell group. The data are expressed as Mean±SD.

Nanobodies with different concentrations were no cytotoxicity to mice (BHK-21 cells), sheep (sheep kidney cells) or cattle (MDBK cells). It indicated that TIM-3 nanobody was not cytotoxic to animal cells.

MTT (thiazolyl blue) might be quantitatively determined by spectrophotometric determination of specific wavelength and thus be used to analyze the cell survival and growth. BioVision's MTS cell proliferation assay kit is a colorimetric method as an updated version of MTT for sensitive quantification of living cells in proliferation and cytotoxicity analyses that might be used to determine whether reagents are toxic to cells. By verifying that the nanobody was not toxic to mammalian cells BHK-21, MDBK or sheep kidney cells, thus it might be safely used in animals.

2.2 NO Activation Experiment Detection

FIG. 24 Shows the effect of TIM-3 on the NO secretion level of immune cells. In FIG. 24, negative refers to control group; PBS refers to PBS group; TIM-3 refers to TIM-3 nanobody group.

After T7 phage was added to the immune cells and incubated with TIM-3 nanobodies with different concentrations for 24 h, it was shown that the enhancement of NO concentration by TIM-3 nanobody was positively correlated with the concentration. The higher the concentration of TIM-3 nanobody was, the higher the NO detection value was, indicating the higher the secretion level of NO. The enhancement effect of TIM-3 nanobody was small with the concentration of 10 µg/ml, 20 µg/ml and 40 µg/ml, and reached its maximum value at 80 µg/ml.

Nitric Oxide (NO), as an intercellular and intracellular signaling substance, plays a role in signal transmission, and is a novel biological messenger molecule. The studies according to Lanzhou veterinary research institute, Chinese academy of agricultural sciences state key laboratory of the ministry of agriculture veterinary pathogenic biology and animal virology laboratory have shown that T7 phage particles is easily swallowed by immune cells and can promote the immune cells being mature and NO cytokine secretion, which can be used as cell model to verify the interaction relationship and intensity of interaction between FMDV and immune cells. The strength of the interaction between immune cells and antigen can be reflected by using a kit to detect the content of NO in the culture medium.

At a high concentration, TIM-3 nanobody has a better ability to promote the secretion of NO by immune cells, thus relieving the inhibition that other immune cells acting on immune cells such as T cells (through the binding of TIM-3 receptor and ligand). The ability to promote immune cells indicates that TIM-3 nanobody can be used to promote the level of animal cell immunity, and can be used as a potential immune adjuvant or immune promoter in the case of virus transmission. TIM-3 immunosuppressive receptors also exist in other immune-related cells, and blocking immune checkpoints can enhance the activity of immune-related cells.

2.3 Changes in IL-4, IFN-γ Cytokines and NO Secretion in Mice after Nanobody Injection Serum IL-4 cytokine levels in mice were detected with Solarbio IL-4 cytokine detection kit, IFN-γ cytokine detection kit and NO detection kit. The results were shown in the table below. (8 mice were tested in each group, and each data represented the OD450 value detected by 1 mouse.)

| IL-4 | | IFN-γ | | NO | |
|---|---|---|---|---|---|
| PBS | TIM-3 | PBS | TIM-3 | PBS | TIM-3 |
| 0.093 | 0.097 | 0.071 | 0.078 | 0.066 | 0.069 |
| 0.088 | 0.085 | 0.069 | 0.067 | 0.075 | 0.061 |
| 0.08 | 0.07 | 0.076 | 0.067 | 0.072 | 0.065 |
| 0.096 | 0.085 | 0.091 | 0.063 | 0.08 | 0.063 |
| 0.093 | 0.087 | 0.077 | 0.061 | 0.073 | 0.07 |
| 0.105 | 0.09 | 0.083 | 0.064 | 0.077 | 0.07 |
| 0.087 | 0.089 | 0.088 | 0.064 | 0.073 | 0.076 |
| 0.124 | 0.093 | 0.12 | 0.066 | 0.082 | 0.073 |

2.4 Protective Tests of *Staphylococcus aureus* and *Streptococcus agalactiae.*

The conditions of 8 mice in each group 24 hours after protective test were shown in the table below.

| | Mice/ eight each group | In good condition/ number | In poor condition/ number | Died/ number |
|---|---|---|---|---|
| *Staphylococcus aureus* | PBS | | 1 | 7 |
| | TIM-3 | 3 | 3 | 2 |
| *Streptococcus agalactiae* | PBS | | 1 | 7 |
| | TIM-3 | 2 | | 6 |

The ability to promote the immune level of mice reveals that TIM-3 nanobody can be used to promote the level of animal cellular immunity, and can be used as a potential immune adjuvant or immune promoter in the case of viral/bacterial transmission for animal protection. TIM-3 immunosuppressive receptors also exist in other immune-related cells. Although many mechanisms have not been clearly revealed, but blocking immune checkpoints can enhance the activity of immune-related cells has been verified. The TIM-3 nanobody prepared in this study can be used to protect animals against *Staphylococcus aureus* and *Streptococcus agalactiae* and enhance the survivals of mice.

The above described are only preferred embodiments of the present application, It should be understood by those skilled in the art that, without departing from the principle of the present application, any variations and modifications fall into the scope of the present application.

SEQUENCE LISTING

<160> NUMBER OF SEQ ID NOS: 4

<210> SEQ ID NO 1
<211> LENGTH: 1049
<212> TYPE: DNA
<213> ORGANISM: Artificial Sequence
<220> FEATURE:
<223> OTHER INFORMATION: TIM-3 nanobody

<400> SEQUENCE: 1
ggtgggcgga acatttcaca agcttaagga gacagtacat atgaaatacc tattgcctac 60
ggcagccgct ggattgttat tactcgcggc ccagccggcc atggcccagg tgcagctgca 120
ggagtctgga ggaggcttgg tgcagcctgg ggggtctctg agactctcct gtgcagcctc 180
tgggttcacc ttccgtagat ctattctgaa atggctccga caggctccag ggaaggaact 240
ggagtgggtg tccactatag atacatactc taataacaca tactatgaag actccttgaa 300
gggccgattc accatctccg cagacaacgc caagaacacg ctgtatctgc aaatggacag 360

| | |
|---|---|
| cctgaaacct gaggacacgg ccgtgtatta ctgtgcaaag ggtggaggtg gtatctactc | 420 |
| ccgcacgtat gactaccggg gccaggggac ccaggtcacc gtctcctcag cggccgcata | 480 |
| cccgtacgac gttccggact acggttccca ccaccatcac catcactaga ctgttgaaag | 540 |
| ttgtttagca aaacctcata cagaaaattc atttactaac gtctggaaag acgacaaaac | 600 |
| tttagatcgt tacgctaact atgagggctg tctgtggaat gctacaggcg ttgtcgtttg | 660 |
| tactggtgac gaaactcagt gttacggtac atgggttcct attgggcttg ctatccctga | 720 |
| aaatgagggt ggtggctctg agggtggcgg ttctgagggt ggcggttctg agggtggcgg | 780 |
| tactaaacct cctgagtacg gtgatacacc tattccgggc tatacttata tcaaccctct | 840 |
| cgacggcact tatccgcctg gtactgagca aaaccccgct aatcctaatc ccttctcttg | 900 |
| aggagtctca gcctcttata ctttcatgtt tcagatatag gttccgaaat aggcaggtgc | 960 |
| attaactgtt atacgggcac tgtactcatg cactgacccc gttaaactta ttaccagtac | 1020 |
| actcctgtat catcaaaagc catgtatga | 1049 |

```
<210> SEQ ID NO 2
<211> LENGTH: 30
<212> TYPE: DNA
<213> ORGANISM: Artificial Sequence
<220> FEATURE:
<223> OTHER INFORMATION: forward primer

<400> SEQUENCE: 2
```

| | |
|---|---|
| gacacgaatt cgccaccatg ttcagccacc | 30 |

```
<210> SEQ ID NO 3
<211> LENGTH: 35
<212> TYPE: DNA
<213> ORGANISM: Artificial Sequence
<220> FEATURE:
<223> OTHER INFORMATION: reverse primer

<400> SEQUENCE: 3
```

| | |
|---|---|
| gtgtcaagct ttcacttgtc atcatcatcc ttgta | 35 |

```
<210> SEQ ID NO 4
<211> LENGTH: 4541
<212> TYPE: DNA
<213> ORGANISM: Unknown
<220> FEATURE:
<223> OTHER INFORMATION: pMECS phagemid vector

<400> SEQUENCE: 4
```

| | |
|---|---|
| gagcgcccaa tacgcaaacc gcctctcccc gcgcgttggc cgattcatta atgcagctgg | 60 |
| cacgacaggt ttcccgactg gaaagcgggc agtgagcgca acgcaattaa tgtgagttag | 120 |
| ctcactcatt aggcacccca ggctttacac tttatgcttc cggctcgtat gttgtgtgga | 180 |
| attgtgagcg gataacaatt tcacacagga aacagctatg accatgatta cgccaagctt | 240 |
| gcatgcaaat tctatttcaa ggagacagtc ataatgaaat accattgcc tacggcagcc | 300 |
| gctggattgt tattactcgc ggcccagccg gccatggccc aggtgcagct gcaggagtct | 360 |
| agaggggacc caggtcaccg tctcctcagc ggccgcatac ccgtacgacg ttccggacta | 420 |
| cggttcccac caccatcacc atcactagac tgttgaaagt tgtttagcaa aacctcatac | 480 |
| agaaaattca tttactaacg tctggaaaga cgacaaaact ttagatcgtt acgctaacta | 540 |
| tgagggctgt ctgtggaatg ctacaggcgt tgtggtttgt actggtgacg aaactcagtg | 600 |
| ttacggtaca tgggttccta ttgggcttgc tatccctgaa aatgagggtg gtggctctga | 660 |

```
gggtggcggt tctgagggtg gcggttctga gggtggcggt actaaacctc ctgagtacgg    720
tgatacacct attccgggct atacttatat caaccctctc gacggcactt atccgcctgg    780
tactgagcaa aacccgcta atcctaatcc ttctcttgag gagtctcagc ctcttaatac     840
tttcatgttt cagaataata ggttccgaaa taggcagggt gcattaactg tttatacggg    900
cactgttact caaggcactg accccgttaa aacttattac cagtacactc ctgtatcatc    960
aaaagccatg tatgacgctt actggaacgg taaattcaga gactgcgctt ccattctgg    1020 ctttaatgag gacccattcg tttgtgaata tcaaggccaa tcgtctgacc tgcctcaacc   1080
tcctgtcaat gctggcggcg gctctggtgg tggttctggt ggcggctctg agggtggcgg   1140
ctctgagggt ggcggttctg agggtggcgg ctctgagggt ggcggttccg gtggcggctc   1200
cggttccggt gattttgatt atgaaaaaat ggcaaacgct aataagggg ctatgaccga   1260 aaatgccgat gaaaacgcgc tacagtctga cgctaaaggc aaacttgatt ctgtcgctac   1320
tgattacggt gctgctatcg atggtttcat tggtgacgtt tccggccttg ctaatggtaa   1380
tggtgctact ggtgattttg ctggctctaa ttcccaaatg gctcaagtcg gtgacggtga   1440
taattcacct ttaatgaata atttccgtca atatttacct tctttgcctc agtcggttga   1500
atgtcgccct tatgtctttg gcgctggtaa accatatgaa ttttctattg attgtgacaa   1560
aataaactta ttccgtggtg tcttTgcgtt tctTttatat gttgccacct ttatgtatgt   1620
attttcgacg tttgctaaca tactgcgtaa taaggagtct aataagaat tcactggccg   1680 tcgttTtaca acgtcgtgac tgggaaaacc ctggcgttac ccaacttaat cgccttgcag   1740
cacatccccc tttcgccagc tggcgtaata gcgaagaggc ccgcaccgat cgcccttccc   1800
aacagttgcg cagcctgaat ggcgaatggc gcctgatgcg gtattttctc cttacgcatc   1860
tgtgcggtat ttcacaccgc atataaattg taaacgttaa tattttgtta aaattcgcgt   1920
taaatttttg ttaaatcagc tcatttttta accaataggc cgaaatcggc aaaatccctt   1980
ataaatcaaa agaatagccc gagatagggt tgagtgttgt tccagtttgg aacaagagtc   2040
cactattaaa gaacgtggac tccaacgtca agggcgaaa aaccgtctat cagggcgatg   2100
gcccactacg tgaaccatca cccaaatcaa gtttTtTggg gtcgaggtgc cgtaaagcac   2160
taaatcggaa ccctaaaggg agcccccgat ttagagcttg acggggaaag ccggcgaacg   2220
tggcgagaaa ggaagggaag aaagcgaaag gagcgggcgc tagggcgctg gcaagtgtag   2280
cggtcacgct gcgcgtaacc accacacccg ccgcgcttaa tgcgccgcta cagggcgcgt   2340
actatggttg ctttgacggg tgcactctca gtacaatctg ctctgatgcc gcatagttaa   2400
gccagccccg acacccgcca acacccgctg acgcgccctg acgggcttgt ctgctcccgg   2460
catccgctta cagacaagct gtgaccgtct ccggagctg catgtgtcag aggttTtTcac   2520 cgtcatcacc gaaacgcgcg agacgaaagg gcctcgtgat acgcctattt ttataggtta   2580
atgtcatgat aataatggtt tcttagacgt caggtggcac ttttcgggga aatgtgcgcg   2640
gaacccctat ttgttTatTt ttctaaatac attcaaatat gtatccgctc atgagacaat   2700
aaccctgata aatgcttcaa taatattgaa aaaggaagag tatgagtatt caacatttcc   2760
gtgtcgccct tattccctTt tttgcggcat tttgccttcc tgttTtTtgct cacccagaaa   2820 cgctggtgaa agtaaaagat gctgaagatc agttgggtgc acgagtgggt tacatcgaac   2880
tggatctcaa cagcggtaag atccttgaga gttTtcgccc cgaagaacgt ttTccaatga   2940
tgagcacttt taaagttctg ctatgtggcg cggtattatc ccgtattgac gccgggcaag   3000
```

```
agcaactcgg tcgccgcata cactattctc agaatgactt ggttgagtac tcaccagtca    3060
cagaaaagca tcttacggat ggcatgacag taagagaatt atgcagtgct gccataacca    3120
tgagtgataa cactgcggcc aacttacttc tgacaacgat cggaggaccg aaggagctaa    3180
ccgctttttt gcacaacatg ggggatcatg taactcgcct tgatcgttgg gaaccggagc    3240
tgaatgaagc cataccaaac gacgagcgtg acaccacgat gcctgtagca atggcaacaa    3300
cgttgcgcaa actattaact ggcgaactac ttactctagc ttcccggcaa caattaatag    3360
actggatgga ggcggataaa gttgcaggac cacttctgcg ctcggccctt ccggctggct    3420
ggtttattgc tgataaatct ggagccggtg agcgtgggtc tcgcggtatc attgcagcac    3480
tggggccaga tggtaagccc tcccgtatcg tagttatcta cacgacgggg agtcaggcaa    3540
ctatggatga acgaaataga cagatcgctg ataggtgcc tcactgatt aagcattggt     3600
aactgtcaga ccaagtttac tcatatatac tttagattga tttaaaactt cattttaat    3660
ttaaaaggat ctaggtgaag atcctttttg ataatctcat gaccaaaatc ccttaacgtg    3720
agttttcgtt ccactgagcg tcagacccccg tagaaaagat caaggatct tcttgagatc    3780
cttttttct gcgcgtaatc tgctgcttgc aaacaaaaaa accaccgcta ccagcggtgg     3840
tttgtttgcc ggatcaagag ctaccaactc ttttccgaa ggtaactggc ttcagcagag    3900
cgcagatacc aaatactgtc cttctagtgt agccgtagtt aggccaccac ttcaagaact    3960
ctgtagcacc gcctacatac ctcgctctgc taatcctgtt accagtggct gctgccagtg    4020
gcgataagtc gtgtcttacc gggttggact caagacgata gttaccggat aaggcgcagc    4080
ggtcgggctg aacggggggt tcgtgcacac agcccagctt ggagcgaacg acctacaccg    4140
aactgagata cctacagcgt gagcattgag aaagcgccac gcttcccgaa gggagaaagg    4200
cggacaggta tccggtaagc ggcagggtcg gaacaggaga gcgcacgagg gagcttccag    4260
ggggaaacgc ctggtatctt tatagtcctg tcgggtttcg ccacctctga cttgagcgtc    4320
gatttttgtg atgctcgtca gggggggcgga gcctatggaa aaacgccagc aacgcggcct    4380
ttttacggtt cctggccttt tgctggcctt ttgctcacat gttctttcct gcgttatccc    4440
ctgattctgt ggataaccgt attaccgcct ttgagtgagc tgataccgct cgccgcagcc    4500
gaacgaccga gcgcagcgag tcagtgagcg aggaagcgga a                       4541
```

What is claimed is:

1. A nanobody, wherein the nanobody is a T-cell immunoglobulinandmucin-3 (TIM-3) nanobody, wherein a nucleotide sequence encoding the TIM-3 nanobody consists of SEQ ID NO: 1.

2. A method for using a T-cell immunoglobulinandmucin-3 (TIM-3) nanobody encoded by a nucleotide sequence consisting of SEQ ID NO: 1 as a reagent for enhancing immune response of a subject, wherein the method comprises blocking TIM-3 immunosuppressive receptors for enhancing activity of immune-related cells.

* * * * *